(12) United States Patent
Chung et al.

(10) Patent No.: US 10,508,140 B2
(45) Date of Patent: Dec. 17, 2019

(54) PEPTIDE HAVING HAIR GROWTH-PROMOTING ACTIVITY AND/OR MELANIN GENERATION-PROMOTING ACTIVITY, AND USE THEREOF

(71) Applicant: CAREGEN CO., LTD., Anyang-si (KR)

(72) Inventors: Yong Ji Chung, Yongin-si (KR); Eun Mi Kim, Yongin-si (KR); Eung-Ji Lee, Anyang-si (KR)

(73) Assignee: CAREGEN CO., LTD., Anyang-si (KR)

( * ) Notice: Subject to any disclaimer, the term of this patent is extended or adjusted under 35 U.S.C. 154(b) by 0 days.

(21) Appl. No.: 15/999,760

(22) PCT Filed: Feb. 15, 2017

(86) PCT No.: PCT/KR2017/001650
§ 371 (c)(1),
(2) Date: Aug. 20, 2018

(87) PCT Pub. No.: WO2017/142305
PCT Pub. Date: Aug. 24, 2017

(65) Prior Publication Data
US 2019/0071478 A1    Mar. 7, 2019

(30) Foreign Application Priority Data
Feb. 18, 2016    (KR) .................... 10-2016-0019322

(51) Int. Cl.
| | |
|---|---|
| A61K 38/08 | (2019.01) |
| C07K 14/47 | (2006.01) |
| A61K 8/64 | (2006.01) |
| C07K 7/06 | (2006.01) |
| A61Q 7/00 | (2006.01) |
| A61P 17/00 | (2006.01) |

(52) U.S. Cl.
CPC ............ *C07K 14/4705* (2013.01); *A61K 8/64* (2013.01); *A61K 38/08* (2013.01); *A61P 17/00* (2018.01); *A61Q 7/00* (2013.01); *C07K 7/06* (2013.01)

(58) Field of Classification Search
None
See application file for complete search history.

(56) References Cited

U.S. PATENT DOCUMENTS

| | | |
|---|---|---|
| 2011/0263508 A1 | 10/2011 | Kleinig et al. |
| 2014/0364378 A1 | 12/2014 | Chueh et al. |
| 2017/0051014 A1 | 2/2017 | Chung et al. |

FOREIGN PATENT DOCUMENTS

| | | |
|---|---|---|
| EP | 2474555 A1 | 7/2012 |
| EP | 3428177 A2 | 1/2019 |
| JP | 2008-515815 A | 5/2008 |
| JP | 2009-126844 A | 6/2009 |
| KR | 10-2014-0107784 A | 9/2014 |
| KR | 10-2015-0130615 A | 11/2015 |
| WO | WO-2005/082395 A1 | 9/2005 |
| WO | WO-2015/174599 A1 | 11/2015 |

OTHER PUBLICATIONS

GenBank entry KZX83772, uploaded May 2, 2016.*
GenBank entry PWW77566, uploaded May 31, 2018.*
International Search Report dated Jun. 7, 2017 for International Patent Application No. PCT/KR2017/001650, Chung et al., "Peptide Having Hair Growth-Promoting Activity and/or Melanin Generation-Promoting Activity, and Use Thereof," filed Feb. 15, 2017 (6 pages).
Extended European Search Report dated Feb. 14, 2019 for European Patent Application No. 17753466.6, Chung et al., "Peptide Having Hair Growth-Promoting Activity and/or Melanin Generation-Promoting Activity, and Use Thereof," filed Feb. 15, 2017 (10 pages).

\* cited by examiner

*Primary Examiner* — Fred H Reynolds
(74) *Attorney, Agent, or Firm* — Clark & Elbing LLP; Susan M. Michaud

(57) ABSTRACT

The present invention provides: a peptide which shows a hair growth-promoting activity and/or a melanin generation-promoting activity; a composition for preventing and/or alleviating hair loss, comprising the peptide as an effective ingredient; a composition for promoting hair growth, comprising the peptide as an effective ingredient; a use of the peptide for preventing and/or alleviating hair loss; a use of the peptide for promoting hair growth; a pharmaceutical composition for preventing and/or treating hypomelanosis, comprising the peptide as an effective ingredient; a cosmetic composition for preventing and/or treating hypomelanosis, comprising the peptide as an effective ingredient; and a use of the peptide for preventing and/or treating hypomelanosis.

22 Claims, 28 Drawing Sheets
Specification includes a Sequence Listing.

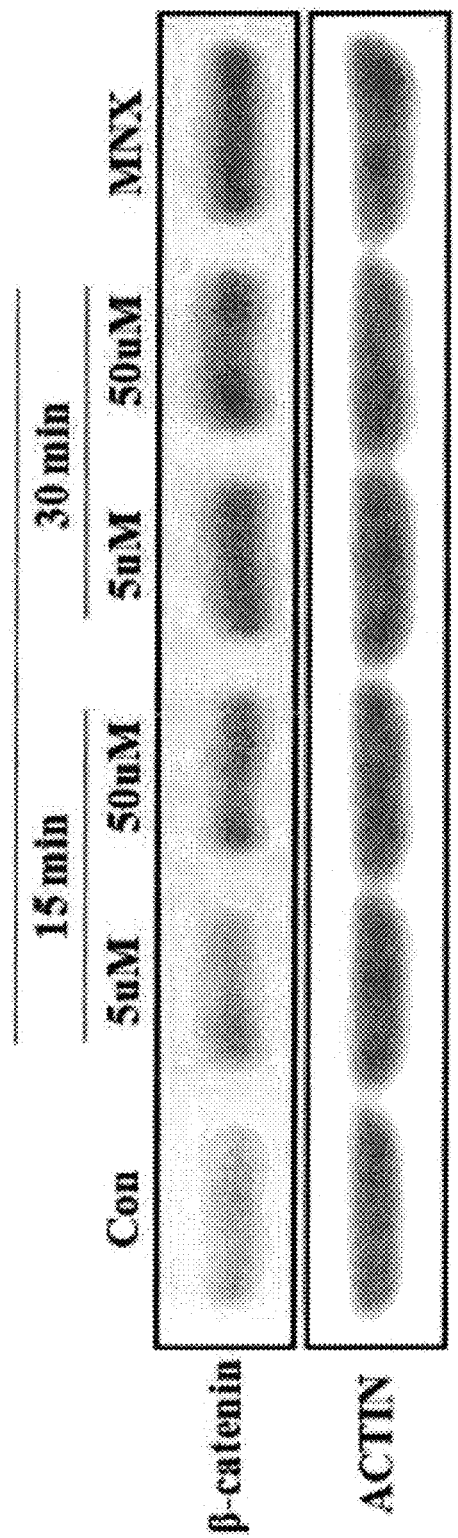

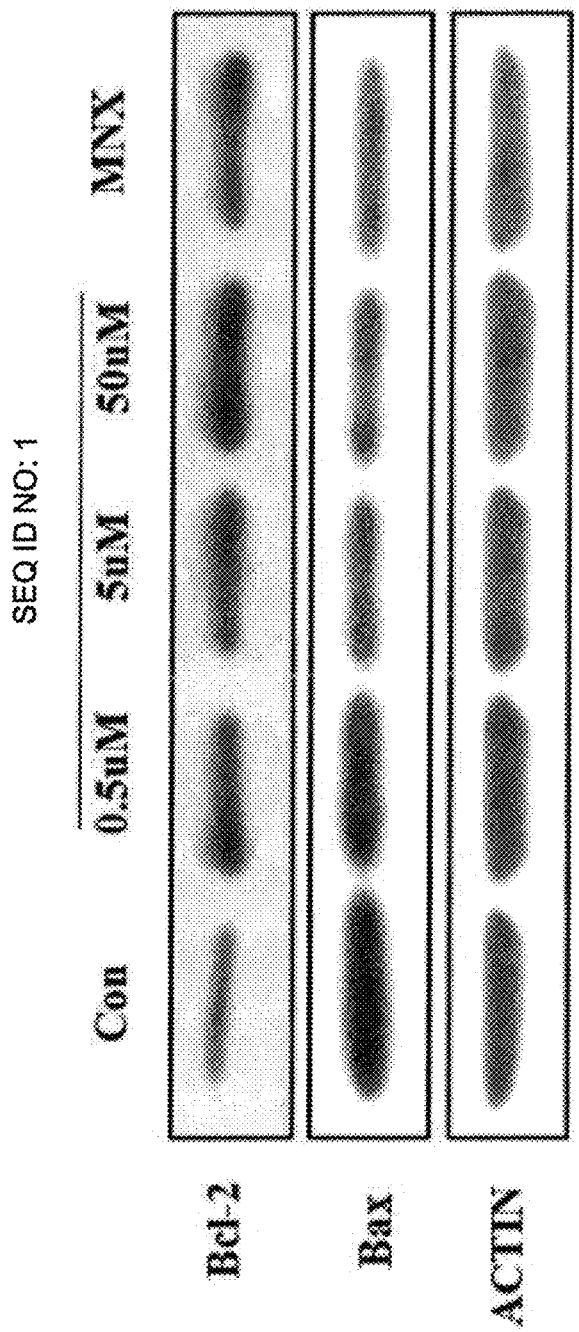

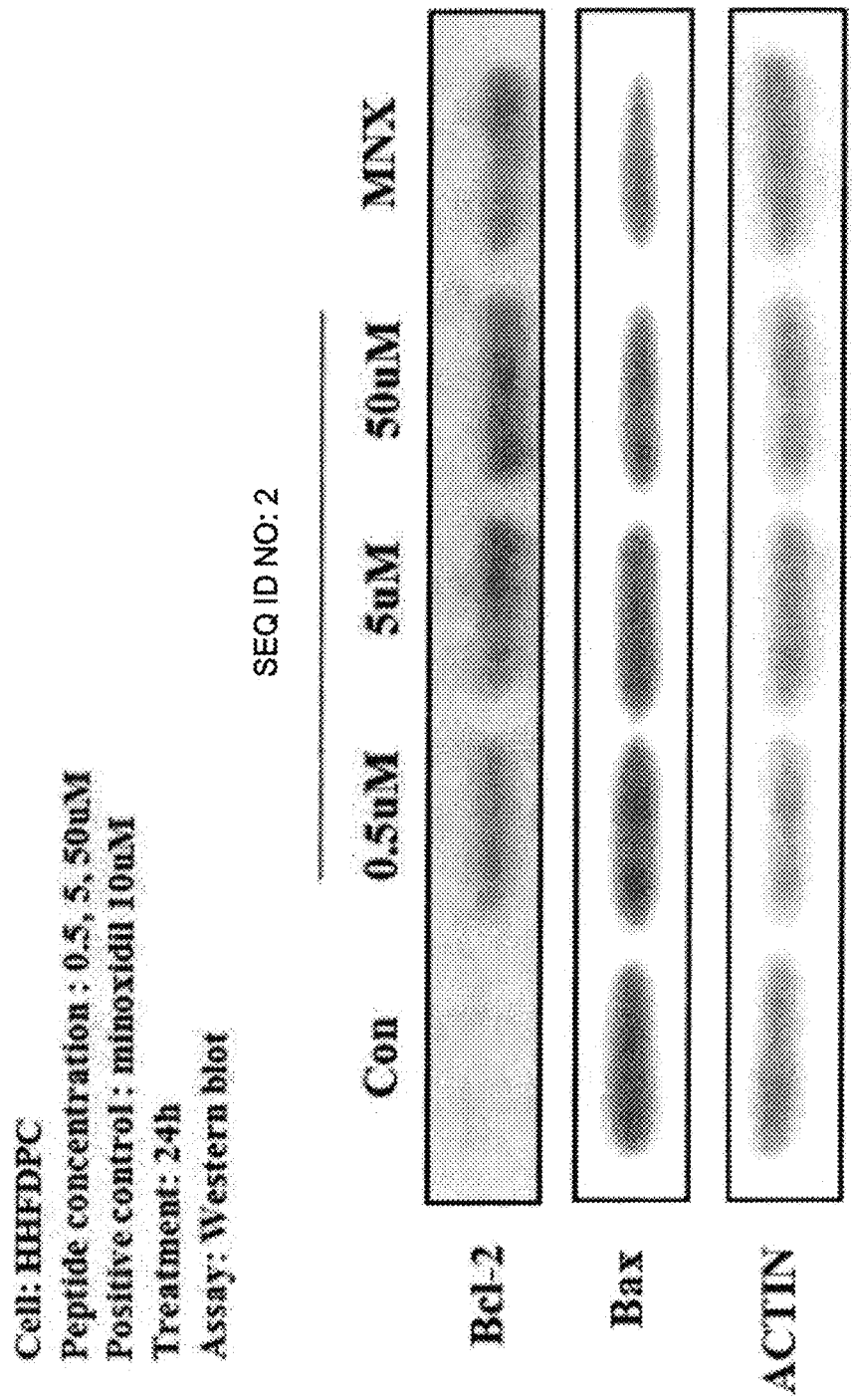

Fig. 8a

Cell: HaCaT
Peptide concentration: 0.5, 5, 50uM
Positive control: RT-PCR
Treatment: 24h
Assay: RT-PCR

SEQ ID NO: 1

Con | 0.5uM | 5uM | 50uM | EGF

Ha3-II
Keratin-14
GAPDH

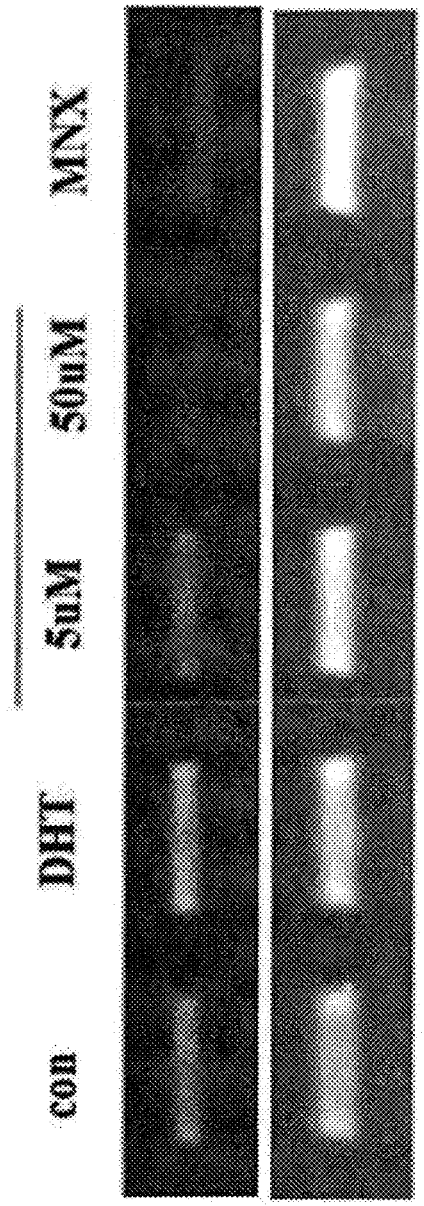

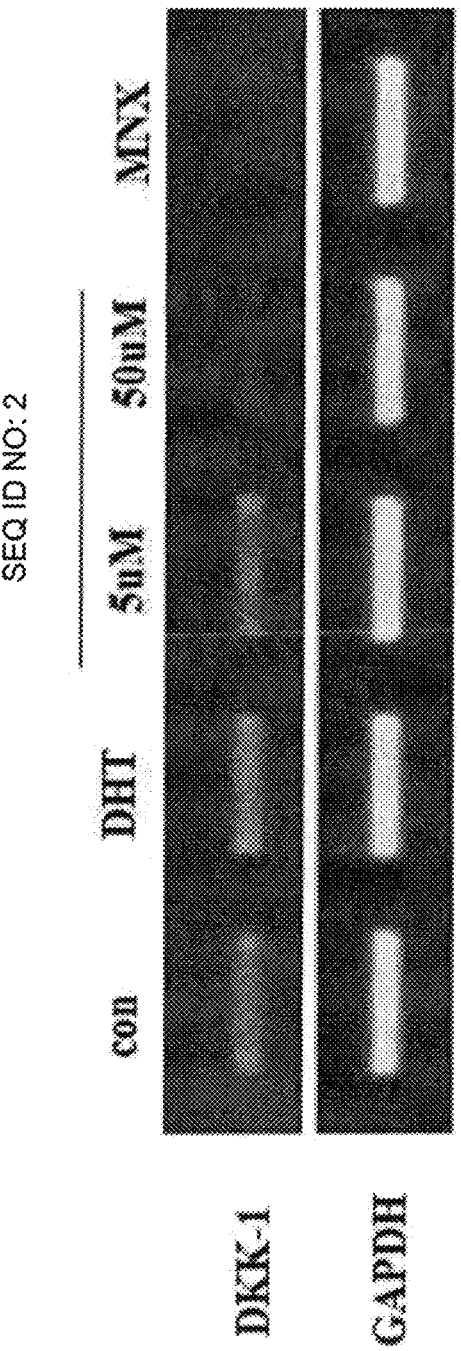

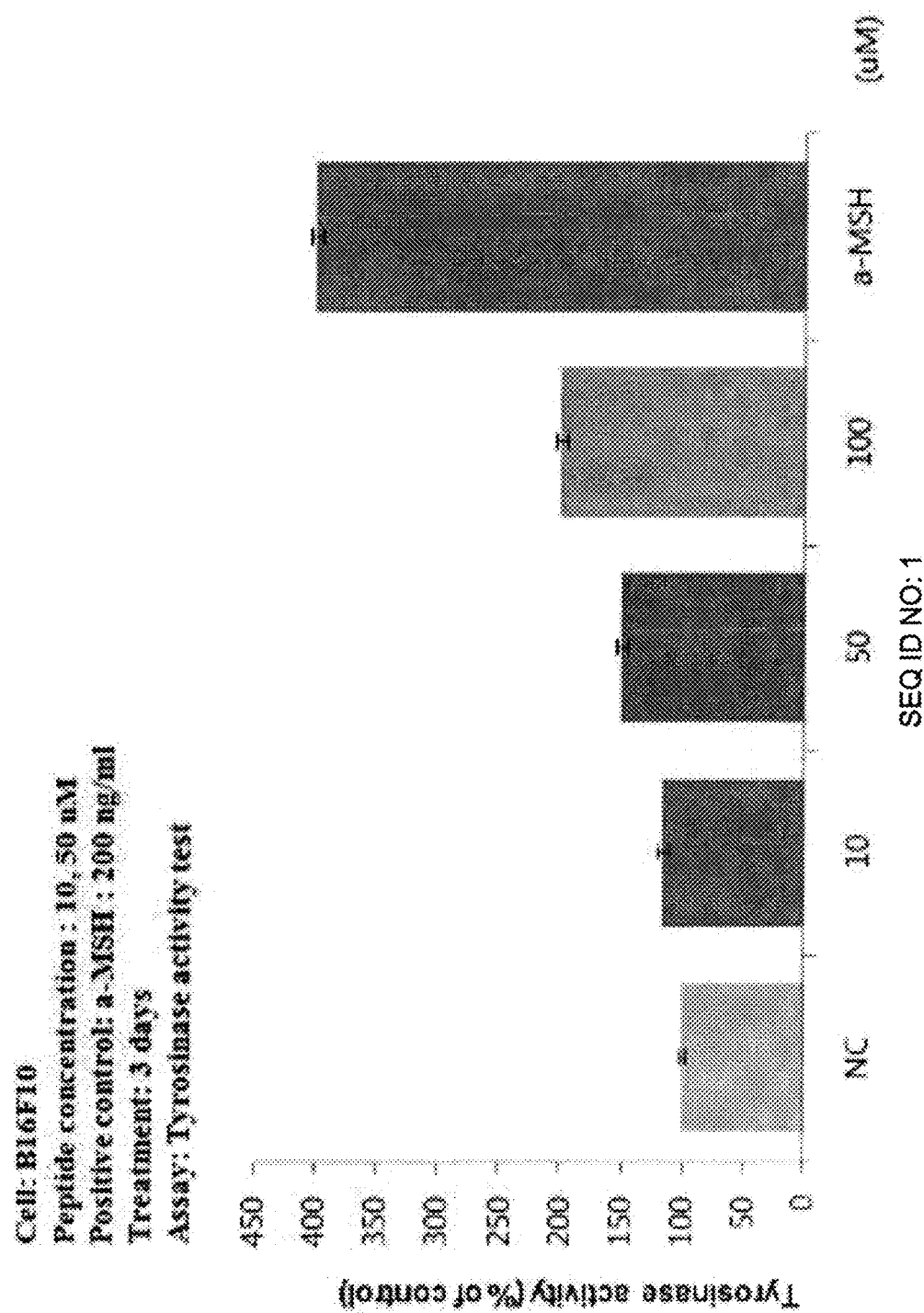

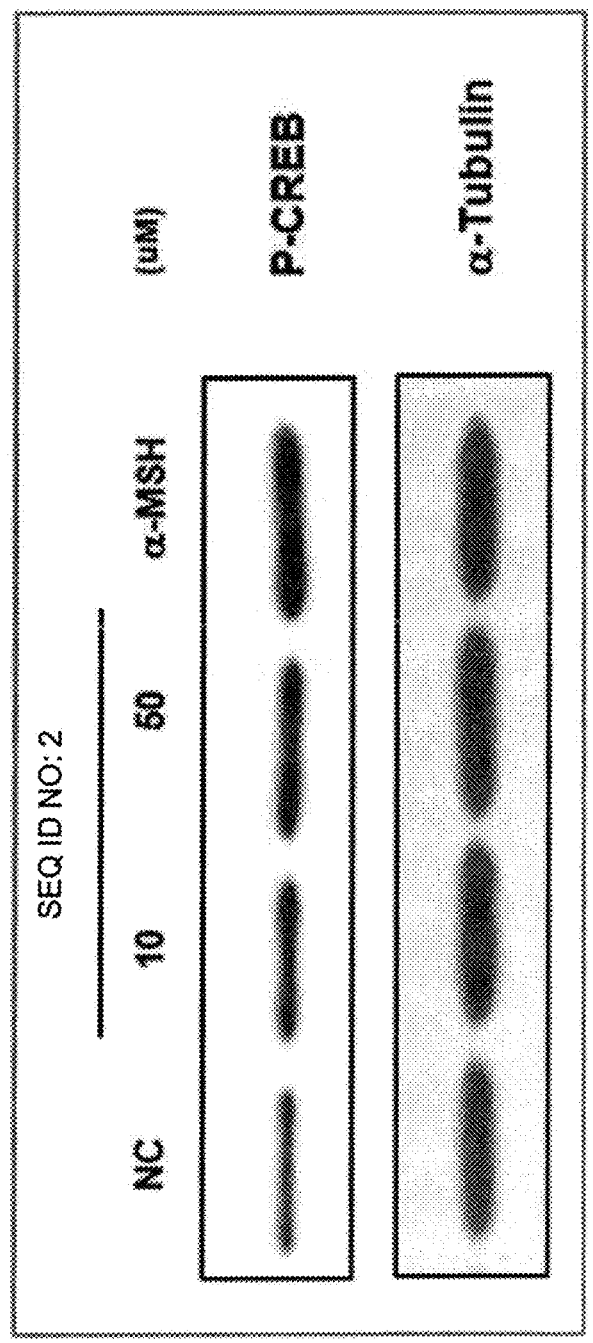

PEPTIDE HAVING HAIR GROWTH-PROMOTING ACTIVITY AND/OR MELANIN GENERATION-PROMOTING ACTIVITY, AND USE THEREOF

TECHNICAL FIELD

The present invention relates to a peptide having an activity to stimulate hair production and/or melanogenesis, a composition containing the peptide as an active ingredient for preventing and/or improving hair loss, a composition containing the peptide as an active ingredient for stimulating hair production and/or hair growth, a use of the peptide for preventing and/or improving hair loss, a use of the peptide for stimulating hair production and/or hair growth, a pharmaceutical composition containing the peptide as an active ingredient for preventing and/or treating hypomelanosis, a cosmetic composition containing the peptide as an active ingredient for preventing and/or improving hypomelanosis, and a use of the peptide for preventing, improving and/or treating hypomelanosis.

BACKGROUND ART

The hair follicle, which is grown from a lower part of the primitive epidermis and extends into a deeper skin layer, is a distinctive organ found in mammalian skin. A cell plug known as a follicle or dermal papilla cell exists in the base of the hair follicle (Stenn and Paus, *Physiol. Rev.*, 81: 449 (2002)), and the papilla is essential in the normal circulation of the hair follicle (Oliver, *Embryol. Exp. Morph.* 15: 3311 (1966); and Oliver, *Embryol. Exp. Morph.* 16: 231 (1966)) and the growth of the hair shaft. The hair shaft is a thread-shaped structure formed of epithelial cells composed of keratin filaments and filament-aggregating proteins tightly attached thereto.

Human hairs fall out and again produce while cyclically repeating anagen, catagen, and telogen phases. The cycle of growth in the hair cycle is determined by regulation of hormones or other growth factors. Severe stress or malnutrition may advance the catagen and telogen phases, leading to severe hair loss (*American Journal of Pathology*, 162(3) (2003), (Arck, Petra Clara; Handjiski, Bori)).

In cases of male-pattern baldness, the hair follicles at the front and top of the scalp are sensitive to androgen. Thus, male-pattern baldness corresponds to the minimization of hair follicles rather than the destruction of hair follicles, and is caused by excessive secretion of the male hormone androgen. The excessive secretion of androgen results in the activation of 5-α reductase, converting testosterone into dihydrotestosterone (DHT). The resulting dihydrotestosterone shortens the cycle of hair growth and miniaturizes hair follicles, decreasing the number of thick strong adult hairs, leading to hair loss.

In general, hair loss increases with aging. For example, different disorders, such as cicatricial alopecia or scar conditions associated with burns or compression injury, may cause severe hair loss. Several substances as medicaments have been used to treat such a hair loss phenomenon, but the medicaments are expensive or cause several adverse effects.

In addition, these medicaments have drawbacks in that the sustained use thereof is required; hair loss again occurs when the use thereof is stopped; there are individual differences in efficacy; and side effects vary from person to person.

Furthermore, raw materials used as cosmetics have an advantage of being inexpensive, but their efficacy is not great since they contain ingredients derived from plant extracts. Therefore, there is an increasing need in the art for novel effective ingredients that are more economical in terms of costs.

Two available drugs known so far (minoxidil and finasteride) might delay additional hair loss, but do not induce the regeneration of new hair follicles. Among hair cosmetics, a lot of anti-hair loss products using plant extracts and the like have also been released.

For example, the products using plant extracts and the like that have been developed include: products containing extracts of *sophora* root, chili pepper, swertia, *morus* bark, *morus* leaves, *ginseng*, licorice, peony, foxglove, fennel, *cornus* fruit, garlic, and the like; products wherein a composition containing xanthines and growth hormones is added to improve cellular metabolism suppressed by excessive dihydrotestosterone and stimulate hair growth induced by growth hormones, thereby preventing hair loss and attaining hair production, leading to a hair growth stimulating effect; hair production stimulating products that supply nutrients to the scalp and hair through the development of products containing minerals, vitamins, and extracts of green tea, rosemary, mugwort, or licorice, in order to stimulate hair production and hair growth, and have effects in the prevention of hair loss and the stimulation of hair growth; and products for male-pattern baldness wherein the substances, such as vitamin B, vitamin C, vitamin D, vitamin E, nicotinic acid, pantothenic acid, biotin, and folic acid, are mixed with plant extracts to inhibit 5-α reductase, thereby preventing the production of dihydrotestosterone in the metabolism of male hormones and helping hair metabolism. However, products that affect even the production of new hair are difficult to find.

Skin cells produce melanin in melanosomes of melanocytes that are present in the basal epidermal layer, as a defense mechanism for the stimulation of ultraviolet light, environmental pollution, and other external factors. Melanin is an important factor to determine the color of skin, eyes, and hair of animals. Hypomelanosis is also known as a risk factor of skin cancer.

Asians are sensitive to the overproduction of melanin, and thus many whitening-related studies for melanogenesis inhibition have been conducted. In recent years, the demand against vitiligo, which is caused by melanogenesis inhibition, is also increasing, and thus studies therefor are being conducted.

Vitiligo is an acquired decolorizing disease wherein milky spots of several sizes and shapes are shown due to apoptosis or necrosis of melanocytes.

Vitiligo is a relatively common disease that occurs in about 1% of the population around the world, and there is no difference in the disease by race or area. Regarding the occurrence ages, vitiligo occurs most frequently at ages of 10 to 30 years, with 95% occurring before the age of 40, and 30% of the patients have a family history.

The causes of vitiligo have not yet been accurately revealed, but there are various theories, such as autoimmune hypothesis, neural hypothesis, and melanocyte self-destruct hypothesis. The autoimmune hypothesis is that the destruction or dysfunction of melanocytes is caused by the expression of auto-antibodies to melanocytes-based antigens, or melanocytes are destroyed by lymphokines secreted by cytotoxic lymphocytes or activated lymphocytes. The neural hypothesis is that hydrogen peroxide associated with stress is generated due to abnormal catecholamine biosynthesis and increased monoamine oxidase, resulting in the destruction of melanocytes, and vitiligo may occur along the ganglion or vitiligo may occur after nerve damage or stress. The melanocytes self-destruct hypothesis is that intermediate metabolites or phenol complexes as final metabolite of the melanogenic process are accumulated in melanocytes, resulting in cell destruction. Besides, various factors, such as inherent cellular defects, genetic factors, apoptosis, calcium metabolic disorders, are suggested.

Melanin is synthesized from melanocytes, and plays an important role in skin protection by the irradiation of UV light or the absorption of toxic substances and chemical substances. Therefore, people having no occurrence of normal melanin synthesis have an appearance problem in that the skin becomes white in part rather than whole, causing spots, and have a severe problem of being sensitive to external stimulations.

Tyrosinase, tyrosinase related protein-1 (TRP-1), and tyrosinase related protein-2 (TRP-2), which are important enzymes in melanin synthesis, act as catalysts for oxidative reactions (Pigment Cell Res. 14 (6): 43744).

Here, tyrosinase acts to oxidize tyrosine into L-3,4-dihydroxyphenylalanine (DOPA) and DOPA into DOPA quinine, and TRP-1 is dihydroxyindole carboxylic acid oxidase and involved in the conversion of 5,6-dihydroxyindole-2-carboxylic acid (DHICA) into indol-5,6-quinone-2-carboxylic acid.

TRP-1 also serves to stabilize tyrosinase and regulate activity thereof. TRP-2, which is the DOPA chrome tautomerase, converts DOPA chrome into DHICA to form eumelanon and pheomelanon, constituting melanocytes, and the ratio thereof determines the colors of skin, hair, eyes, and the like.

The melanin synthesis is activated by UV irradiation and -melanocyte stimulating hormone (MSH). Here, $\alpha$-MSH, which is a peptide hormone, is known to be produced by ultraviolet light and made from several cells including those of the pituitary gland and skin.

Here, $\alpha$-MSH acts on melanocortin receptors (MCR) of melanocytes by paracrine to regulate the activity of the transcription factor microphthalmia-associated transcription factor (MITF), thereby regulating the activity of tyrosinase, DHICA oxidase (TRP-1), DOPAchrometautomerase (TRP-2), and the like, which play important roles in melanin synthesis (THE JOURNAL OF BIOLOGICAL CHEMISTRY Vol. 273, No. 31, Issue of July 31, pp. 195609565, 1998).

It has been reported that the stimulation of melanocytes by UV or $\alpha$-MSH leads to the activation of tyrosinase by p38 or protein kinase A (PKA), respectively. In these two pathways, especially, the $\alpha$-MSH->cAMP->PKA pathway plays an important role in melanin synthesis. The increase in cAMP stimulates the phosphorylation of cAMP-responsive element binding protein (CREB), increasing the expression of the transcription factor MITF, which enhances the activity of tyrosinase and increases the mRNA expression of tyrosinase (Nucleic Acids Res. 30 (14): 3096106, Pigment Cell Melanoma Res 21 (6): 66576).

Asian people including Koreans want to have light skin colors, and thus have conducted many studies about whitening components inhibiting melanogenesis. However, melanin is synthesized from melanocytes in the skin, and plays an important role in skin protection by the irradiation of UV or the absorption of toxic substances and chemical substances. Since the absence of normal synthesis of melanin makes the skin sensitive to external stimulation and shows abnormal external appearances, the treatment for normal melanin synthesis is needed and studies therefor have been also conducted. So far, the development of techniques for stimulating melanin synthesis has not been sufficiently conducted.

DETAILED DESCRIPTION OF THE INVENTION

Technical Problem

The present inventors endeavored to develop peptides having biologically effective activity, and as a result, the present inventors confirmed that a peptide comprising an amino acid sequence of SEQ ID NO: 1 or SEQ ID NO: 2 has excellent hair producing efficacy and melanogenesis stimulating activity and established that these peptides can be favorably used in the prevention or improvement of hair loss and the prevention and treatment of hypomelanosis, and thus the present inventors completed the present invention.

Therefore, an aspect of the present invention is to provide a peptide having an activity to stimulate hair production, the peptide consisting of the amino acid sequence of SEQ ID NO: 1 or SEQ ID NO: 2.

Another aspect of the present invention is to provide a composition for preventing and/or improving hair loss, the composition comprising, as an active ingredient, at least one peptide selected from the group consisting of peptides consisting of the amino acid sequences of SEQ ID NO: 1 and SEQ ID NO: 2.

Still another aspect of the present invention is to provide a composition for stimulating hair production and/or hair growth, the composition comprising, as an active ingredient, at least one peptide selected from the group consisting of peptides consisting of the amino acid sequences of SEQ ID NO: 1 and SEQ ID NO: 2.

Still another aspect of the present invention is to provide a peptide having an activity to stimulate melanogenesis, the peptide consisting of the amino acid sequence of SEQ ID NO: 1 or SEQ ID NO: 2.

Still another aspect of the present invention is to provide a pharmaceutical composition for preventing and/or treating hypomelanosis, the pharmaceutical composition comprising, as an active ingredient, at least one peptide selected from the group consisting of peptides consisting of the amino acid sequences of SEQ ID NO: 1 and SEQ ID NO: 2.

Still another aspect of the present invention is to provide a cosmetic composition for preventing and/or improving hypomelanosis, the cosmetic composition comprising, as an active ingredient, at least one peptide selected from the group consisting of peptides consisting of the amino acid sequences of SEQ ID NO: 1 and SEQ ID NO: 2.

Technical Solution

The present inventors endeavored to develop peptides having biologically effective activity, and as a result, the present inventors confirmed that a peptide comprising an amino acid sequence of SEQ ID NO: 1 or SEQ ID NO: 2 has excellent hair producing efficacy and melanogenesis stimulating activity and established that these peptides can be favorably used in the prevention or improvement of hair loss and the prevention and treatment of hypomelanosis.

The peptide of the present invention is obtained by screening peptides, which have excellent melanogenesis stimulating effects, from peptide libraries possessed by the present inventors, through experiments about gene and protein expression changes or the like, and a total of two types of peptides are provided as a peptide of the present invention.

An aspect of the present invention is directed to a peptide having an activity to stimulate hair production, the peptide comprising an amino acid sequence of SEQ ID NO: 1 or SEQ ID NO: 2.

The peptide may contain an amino acid sequence of SEQ ID NO: 1 or SEQ ID NO: 2, and for example, may be a peptide consisting of the amino acid sequence of SEQ ID NO: 1 or SEQ ID NO: 2.

The peptide of the present invention may have a modification induced at the N-terminal or C-terminal thereof in order to select a part of an amino acid sequence and increase the activity thereof.

For example, the C-terminal modification may be a modification of the C-terminal of the peptide into a hydroxy group (—OH), an amino group (—NH$_2$), an azide group (—NHNH$_2$), or the like, but is not limited thereto.

In addition, the N-terminal modification may be an attachment of at least one protecting group selected from the group consisting of an acetyl group, a fluorenyl methoxy carbonyl group, a formyl group, a palmitoyl group, a myristyl group, a stearyl group, and polyethylene glycol (PEG) to the N-terminal of the peptide, but is not limited thereto. The protecting group protects the peptide of the present invention from in vivo protein cleavage enzymes.

The N-terminal and/or C-terminal modification of the peptide improves the stability of the peptide, and this modification allows the peptide of the present invention to have an increased half-life at the time of in vivo administration, thereby having a high half-life.

According to an aspect of the present invention, the peptide of the present invention stimulates the growth of hair follicle cells, increases the expression of β-catenin as a hair growth-related factor, increases the expression of keratinocyte growth factor (KGF) and vascular endothelial growth factor (VEGF) as hair growth-related growth factors, increases the expression of phosphoinositide 3-kinase (PI3K) as a hair growth signaling molecule, increases the phosphorylation of extracellular signal-regulated kinase (ERK), increases the expression of MSX2, Ha3-II, and keratin-14 as hair growth-related factors, decreases the expression of TGF-β1 and DKK-1 associated with hair growth delay, and induces an increase in expression of Bcl-2 as an apoptosis inhibiting protein and a decrease in expression of Bax as an apoptosis-related protein.

These results indicate that the peptide of the present invention has an excellent effect on hair production. Therefore, the peptide of the present invention can be used for the prevention and/or improvement of hair loss and the stimulation of hair production and/or hair growth.

Another aspect of the present invention is directed to a composition for preventing and/or improving hair loss, the composition comprising, as an active ingredient, at least one peptide selected from the group consisting of peptides consisting of the amino acid sequences of SEQ ID NO: 1 and SEQ ID NO: 2.

The peptide of the present invention induces the proliferation of cells present in hair follicles of skin tissue so as to produce hair roots, leading to the production of new hair follicles. Furthermore, the peptide of the present invention activates β-catenin signals to express hair production stimulating genes and increase the expression of growth factors.

The peptide of the present invention promotes the anagen phase during which hair is produced and grown, exhibits a hair loss inhibiting effect by maintaining the cycle of hair, which proceeds to the catagen phase due to several environmental factors, at the anagen phase, and keeps healthy hair by providing nutrients to normal hair. Therefore, the composition of the present invention is very effective in the prevention and/or improvement of hair loss.

Since the composition of the present invention contains the foregoing peptide of the present invention as an active ingredient, the descriptions of overlapping contents therebetween will be omitted to avoid excessive complexity of the present specification.

Still another aspect of the present invention is directed to a composition for stimulating hair production and/or hair growth, the composition comprising, as an active ingredient, at least one peptide selected from the group consisting of peptides consisting of the amino acid sequences of SEQ ID NO: 1 and SEQ ID NO: 2.

The composition of the present invention may be prepared into a cosmetic composition, but is not limited thereto.

The cosmetic composition of the present invention may contain a cosmetically effective amount of the peptide of the present invention.

In addition, the cosmetic composition may further contain a cosmetically acceptable carrier, but is not limited thereto.

The cosmetic composition of the present invention may be formulated into any dosage form that is conventionally prepared, and examples thereof may include a solution, a suspension, an emulsion, a paste, a gel, a cream, a lotion, a powder, a soap, a surfactant-containing cleanser, an oil, a powder foundation, an emulsion foundation, a wax foundation, and a spray, but are not limited thereto. For example, the cosmetic composition of the present invention may be prepared in a dosage form of emollient lotion, nourishing lotion, nourishing cream, massage cream, essence, eye cream, cleansing cream, cleansing foam, cleansing water, pack, spray, and/or powder.

In cases where the dosage form of the cosmetic composition is a paste, cream, or gel, useful examples of the carrier ingredient may include an animal oil, a plant oil, wax, paraffin, starch, tragacanth, a cellulose derivative, polyethylene glycol, silicone, bentonite, silica, talc, or zinc oxide, but is not limited thereto.

In cases where the dosage form of the cosmetic composition is a powder or spray, lactose, talc, silica, aluminum hydroxide, calcium silicate, or a polyamide powder may be used as a carrier ingredient, but is not limited thereto.

In cases where the dosage form of the cosmetic composition is a spray, the spray may further contain a propellant, such as chlorofluorohydrocarbon, propane/butane, and/or dimethyl ether, but is not limited thereto.

In cases where the dosage form of the cosmetic composition is a solution or emulsion, a solvent, solubilizer, or emulsifier may be used as a carrier component, and examples thereof include water, ethanol, isopropanol, ethyl carbonate, ethyl acetate, benzyl alcohol, benzyl benzoate, propylene glycol, 1,3-butyl glycol oil, glycerol aliphatic esters, polyethylene glycol, or fatty acid esters of sorbitan, but are not limited thereto.

In cases where the dosage form of the cosmetic composition is a suspension, useful examples of the carrier ingredient may include a liquid diluent (such as water, ethanol, or propylene glycol), a suspending agent (such as ethoxylated isostearyl alcohol, polyoxyethylene sorbitol ester, or polyoxyethylene sorbitan ester), microcrystalline cellulose, aluminum metahydroxide, bentonite, agar, or tragacanth, but are not limited thereto.

In cases where the dosage form of the cosmetic composition is a surfactant-containing cleanser, useful examples of the carrier ingredient may be aliphatic alcohol sulfate, aliphatic alcohol ether sulfate, sulfosuccinate monoester, isethionate, imidazolium derivatives, methyl taurate, sarcosinate, fatty acid amide ether sulfate, alkyl amido betaine, aliphatic alcohol, fatty acid glyceride, fatty acid diethanolamide, plant oil, lanoline derivatives, or ethoxylated glycerol fatty acid ester, but are not limited thereto.

The ingredients contained in the cosmetic composition of the present invention may include, in addition to the peptide and carrier ingredients as active ingredients, ingredients ordinarily used in cosmetic compositions, for example, ordinary supplements, such as an antioxidant, a purifier, a solubilizer, vitamins, a pigment and/or a flavoring agent, but are not limited thereto.

Still another aspect of the present invention is directed to a use of a peptide for preventing and/or improving hair loss, the peptide consisting of the amino acid sequence of SEQ ID NO: 1 or SEQ ID NO: 2.

Since the peptide is the same as the foregoing peptide, the descriptions of overlapping contents therebetween will be omitted to avoid excessive complexity of the present specification.

Still another aspect of the present invention is directed to a use of a peptide for stimulating hair production and/or hair growth, the peptide consisting of the amino acid sequence of SEQ ID NO: 1 or SEQ ID NO: 2.

Since the peptide is the same as the foregoing peptide, the descriptions of overlapping contents therebetween will be omitted to avoid excessive complexity of the present specification.

Still another aspect of the present invention is to provide a peptide having an activity to stimulate melanogenesis, the peptide consisting of the amino acid sequence of SEQ ID NO: 1 or SEQ ID NO: 2.

According to an aspect of the present invention, the peptide of the present invention increases melanogenesis in melanocytes, increases the expression of tyrosinase as a melanogenesis regulating enzyme, increases the expression of MITF and TRP1, which are factors involved in melanogenesis, and increases the phosphorylation of CREB.

These results indicate that the peptide of the present invention has an effect of improving hypomelanosis by increasing melanogenesis. Therefore, the peptide of the present invention can be used for the prevention, improvement, and/or treatment of hypomelanosis.

The hypomelanosis is vitiligo, albinism, nevus depigmentosus, *pityriasis* alba, *pityriasis versicolor*, post-inflammatory depigmentation, morphea, piebaldism, idiopathic guttate hypomelanosis, or leucoderma punctatum, but is not limited thereto.

Still another aspect of the present invention is directed to a pharmaceutical composition for preventing and/or treating hypomelanosis, the pharmaceutical composition comprising, as an active ingredient, at least one peptide selected from the group consisting of peptides consisting of the amino acid sequences of SEQ ID NO: 1 and SEQ ID NO: 2.

The composition of the present invention, when prepared as a pharmaceutical composition, may contain a pharmaceutically effective amount of the foregoing peptide of the present invention.

In addition, the pharmaceutical composition may further contain a pharmaceutically acceptable carrier, but is not limited thereto.

The pharmaceutically acceptable carrier contained in the pharmaceutical composition of the present invention is ordinarily used at the time of formulation, and examples thereof may include, but are not limited to, lactose, dextrose, sucrose, sorbitol, mannitol, starch, acacia gum, calcium phosphate, alginate, gelatin, calcium silicate, microcrystalline cellulose, polyvinylpyrrolidone, cellulose, water, syrup, methyl cellulose, methyl hydroxybenzoate, propyl hydroxybenzoate, talc, magnesium stearate, and/or mineral oil.

The pharmaceutical composition of the present invention may further contain a lubricant, a wetting agent, a sweetening agent, a flavoring agent, an emulsifier, a suspending agent, a preservative, and the like, in addition to the above ingredients.

The pharmaceutical composition of the present invention may be administered parenterally, and for example, may be administered by topical skin administration.

The appropriate dose of the pharmaceutical composition of the present invention varies depending on factors, such as a formulating method, a manner of administration, patient's age, body weight, gender, morbidity, food, a time of administration, a route of administration, an excretion rate, and response sensitivity. The ordinarily skilled practitioners can easily determine and prescribe the dose that is effective for the desired treatment or prevention. According to a preferable embodiment of the present invention, the daily dose of the pharmaceutical composition of the present invention is 0.001-1000 mg/kg.

The pharmaceutical composition of the present invention is formulated using a pharmaceutically acceptable carrier and/or excipient according to a method that is easily conducted by a person having ordinary skills in the art to which the present invention pertains, and the pharmaceutical composition of the present invention may be prepared into a unit dosage form or may be inserted into a multi-dose container.

Here, the dosage form may be a solution in an oily or aqueous medium, a suspension, and/or an emulsion, an extract, a powder, granules, a tablet, a capsule, or a gel (e.g., a hydrogel), and may further contain a dispersing agent and/or a stabilizer.

Still another aspect of the present invention is directed to a cosmetic composition for preventing and/or improving hypomelanosis, the cosmetic composition comprising, as an active ingredient, at least one peptide selected from the group consisting of peptides consisting of the amino acid sequences of SEQ ID NO: 1 and SEQ ID NO: 2.

When the composition of the present invention is prepared as a cosmetic composition, the composition may contain a cosmetically effective amount f the foregoing peptide of the present invention.

In addition, the cosmetic composition may further contain a cosmetically acceptable carrier, but is not limited thereto.

As used herein, the term "peptide" refers to a linear molecule formed of amino acid residues link to each other via peptide linkages. The peptide of the present invention may be prepared by known chemical synthesis methods, especially, solid-phase synthesis techniques (solid-phase synthesis techniques; Merrifield, *J. Amer. Chem. Soc.* 85:2149-54(1963); Stewart, et al., *Solid Phase Peptide Synthesis,* 2nd. ed., Pierce Chem. Co.: Rockford, 111(1984)) or liquid-phase synthesis techniques (U.S. Pat. No. 5,516,891).

As used herein, the term "stability" refers to storage stability (e.g., room-temperature stability) as well as in vivo stability.

As used herein, the term "stimulating hair production" refers to the production of hair, and is used in a broad sense to increase the rate of hair production and the amount of hair production. In addition, the term means that hair root functions are enhanced, or the number of hairs growing in hair follicles increases due to shortening the cycle of hair falling and production.

As used herein, the term "hair growth" refers to increasing the thickness of the generated hair or having an influence on the length increase rate.

As used herein, the term "preventing hair loss" refers to blocking or weakening the fall out of hair from the hair follicles or scalp.

As used herein, the term "cosmetically effective amount" refers to an amount sufficient to attain the efficacy of the foregoing composition of the present invention.

As used herein, the term "pharmaceutically effective amount" refers to an amount sufficient to attain the efficacy or activity of the foregoing peptide.

Advantageous Effects

The present invention is directed to a peptide having an activity to stimulate hair production and/or melanogenesis, a composition containing the peptide as an active ingredient for preventing and/or improving hair loss, a composition containing the peptide as an active ingredient for stimulating hair production and/or hair growth, a use of the peptide for preventing and/or improving hair loss, a use of the peptide for stimulating hair production and/or hair growth, a pharmaceutical composition containing the peptide as an active ingredient for preventing and/or treating hypomelanosis, a cosmetic composition containing the peptide as an active ingredient for preventing and/or improving hypomelanosis, and a use of the peptide for preventing, improving and/or treating hypomelanosis. The peptide stimulates the growth of hair follicle cells and increases the expression of hair production-related growth factors and hair production-related factors, thereby showing an excellent effect on hair production.

In addition, the peptide increases the activity and expression of tyrosinase and increases the expression of factors involved in melanogenesis, thereby showing an excellent effect on melanogenesis. The foregoing peptide of the present invention can be very advantageously applied to medicines, quasi-medicines, and cosmetics through excellent activity and safety thereof

BRIEF DESCRIPTION OF THE DRAWINGS

FIG. 2a is a diagram showing the results of confirming an increase in expression of β-catenin by a peptide composed of the amino acid sequence of SEQ ID NO: 1 according to an embodiment of the present invention.

FIG. 6a is an image showing the results of confirming the inhibition of TGF-β1 expression by a peptide composed of the amino acid sequence of SEQ ID NO: 1 according to an embodiment of the present invention.

FIG. 7a is an image showing the results of confirming an increase of expression of Bcl-2 and a decrease in expression of Bax by a peptide composed of the amino acid sequence of SEQ ID NO: 1 according to an embodiment of the present invention.

FIG. 7b is an image showing the results of confirming an increase in expression of Bcl-2 and a decrease in expression of Bax by a peptide composed of the amino acid sequence of SEQ ID NO: 2 according to an embodiment of the present invention.

FIG. 8a is an image showing the results of confirming increases in expression of Ha3-II and keratin-14 by a peptide composed of the amino acid sequence of SEQ ID NO: 1 according to an embodiment of the present invention.

FIG. 9a is an image of confirming a decrease in mRNA expression of DKK-1 as a hair growth delay related factor, which has been increased by the treatment of human hair follicle dermal papilla cells with DHT, by the treatment with a peptide composed of the amino acid sequence of SEQ ID NO: 1 according to an embodiment of the present invention.

FIG. 9b is an image of confirming a decrease in mRNA expression of DKK-1 as a hair growth delay related factor, which has been increased by the treatment of human hair follicle dermal papilla cells with DHT, by the treatment with a peptide composed of the amino acid sequence of SEQ ID NO: 2 according to an embodiment of the present invention.

FIG. 12a shows the results of confirming the increase of tyrosinase activity by a peptide composed of the amino acid sequence of SEQ ID NO: 1 according to an embodiment of the present invention.

FIG. 15 is an image showing the results of confirming an increase in phosphorylation of CREB by a peptide composed of the amino acid sequence of SEQ ID NO: 2 according to an embodiment of the present invention.

BEST MODE FOR CARRYING OUT THE INVENTION

Figure 1A:
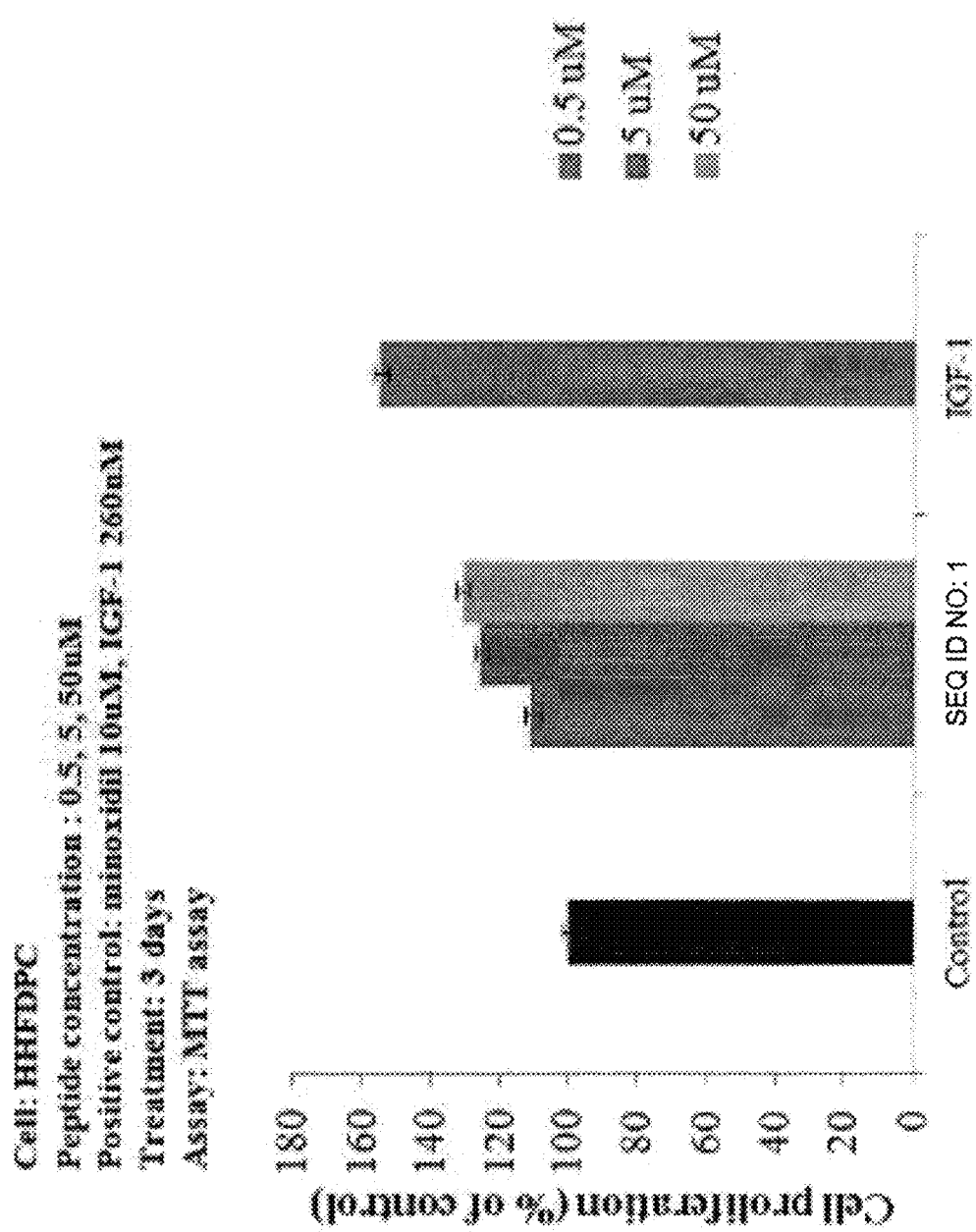
FIG. 1a is a graph showing a human hair follicle dermal papilla cell (HHFDPC) growth stimulating effect of a peptide composed of the amino acid sequence of SEQ ID NO: 1 according to an embodiment of the present invention.

The present invention is directed to a peptide showing hair production stimulating activity, the peptide consisting of the amino acid sequence of SEQ ID NO: 1 or 2.

MODE FOR CARRYING OUT THE INVENTION

Described in detail with reference to examples. These examples are only for illustrating the present invention more specifically, and it will be apparent to those skilled in the art that the scope of the present invention is not limited by these examples.

EXAMPLES

Synthetic Example 1: Peptide Synthesis 700 mg of chlorotrityl chloride resin (CTL resin, Nova Biochem Cat No. 01-64-0021) was added into a reaction container, and 10 ml of methylene chloride (MC) was added, followed by stirring for 3 minutes. After the solution was removed, 10 ml of dimethyl form amide (DMF) was added, followed by stirring for 3 minutes, and then the solvent was again removed.

10 ml of a dichloromethane solution was added to a reactor, and 200 mmole Fmoc-Leu-OH (Bachem, Swiss) and 400 mmole diisopropyl ethylamine (DIEA) were added. Thereafter, the mixture was well dissolved with stirring, and then the reaction was conducted with stirring for 1 hour. After the reaction, washing was conducted, and then methanol and DIEA (2:1) were dissolved in dichloromethane (DCM), followed by reaction for 10 minutes, and then the resulting material was washed with excess DCM/DMF (1:1).

After the solution was removed, 10 ml of dimethyl form amide (DMF) was added, followed by stirring for 3 minutes, and then the solvent was again removed. 10 ml of a deprotection solution (20% piperidine/DMF) was added to a reaction container, followed by stirring at room temperature for 10 minutes, and then the solution was removed. An equal amount of a deprotection solution was added, and then the reaction was again maintained for 10 minutes, and thereafter, the solution was removed, followed by washing twice with DMF, once with MC, and once with DMF, for 3 minutes each, thereby preparing Leu-CTL Resin.

10 ml of a DMF solution was added to a new reactor, and 200 mmol Fmoc-Thr(tBu)-OH (Bachem, Swiss), 200 mmol HoBt, and 200 mmole Bop were added, and the mixture was well dissolved with stirring. 400 mmole DIEA was added to a reactor in two divided portions, and then stirring was conducted for at least 5 minutes until all solids were dissolved. The dissolved amino acid mixed solution was added to the reaction container containing the deprotected resin, and the reaction was conducted with stirring at room temperature for 1 hour.

After the reaction solution was removed, the stirring was conducted using a DMF solution three times for 5 minutes each, followed by removal. A small amount of the reaction resin was taken to check the extent of reaction using the Kaiser test (Ninhydrin test). The deprotection reaction was twice conducted using a deprotection solution in the same manner as described above, thereby preparing Thr(tBu)-Leu-CTL Resin.

After sufficient washing with DMF and MC, the Kaiser test was again conducted, and then the following amino acid attachment test was conducted in the same manner as described above.

A chain reaction was conducted in the order of Fmoc-Asp(OtBu)-OH, Fmoc-Ala-OH, Fmoc-Ser(tBu)-OH, Fmoc-Arg(Pbf)-OH, Fmoc-Trp-OH, Fmoc-Lys(Boc)-OH, and Fmoc-Trp-OH on the basis of the selected amino acid sequence The Fmoc-protecting group was removed by reaction twice with the deprotection solution for 10 minutes for each and then favorable washing.

Acetic anhydride, DIEA, and HoBt were added to conduct acetylation for 1 hour, and then the prepared peptidyl resin was washed with DMF, MC, and methanol three times for each, dried under the flow of nitrogen gas, and completely dried by decompression under vacuum in P205.

Thereafter, 30 ml of a leaving solution [95% trifluoroacetic acid (TFA), 5% distilled water 2, and 5% thioanisole 2] was added, and the reaction was maintained for 2 hours while the mixture was intermittently stirred at room temperature.

The resin was obtained through filtration, washed with a small amount of a TFA solution, and then mixed with the stock solution. The distillation was conducted under reduced pressure to reduce the total volume by half, and then 50 ml of cold ether was added to induce precipitation.

Thereafter, the precipitates were collected by centrifugation, followed by washing twice with cold ether. The stock solution was removed, followed by sufficient drying under nitrogen atmosphere, thereby synthesizing 0.73 g of a peptide of the amino acid sequence of SEQ ID NO: 1 (Trp-Lys-Trp-Arg-Ser-Ala-Asp-Thr-Leu) (yield: 93.1%) prior to purification.

The molecular weight was determined as 1162.3 (theoretical value: 1162.3) by using a molecular weight analysis system. A peptide composed of the amino acid sequence of SEQ ID NO: 2 (Lys-Trp-Arg-Ser-Ala-Asp-Thr-Leu) was also synthesized by the same method as described above.

TABLE 1

| SEQ ID NO | Sequence (5'->3') | Analysis value (Mass spectrometer) | |
|---|---|---|---|
| | | Analytical value | Theoretical value |
| 1 | Trp-Lys-Trp-Arg-Ser-Ala-Asp-Thr-Leu | 1162.3 | 1162.3 |
| 2 | Lys-Trp-Lys-Arg-Ser-Ala-Asp-Thr-Leu | 1104.2 | 1104.26 |

TABLE 2

| SEQ ID NO | Primer name | Sequence (5'-3') |
|---|---|---|
| 3 | KGF_F | TCTGTCGAACACAGTGGTACCT |
| 4 | KGF_R | GTGTGTCCATTTAGCTGATGCAT |
| 5 | VEGF_F | CCATGAACTTTCTGCTGTCTT |
| 6 | VEGF_R | TCGATCGTTCTGTATCAGTCT |

Example 1: DPC Proliferation Assay

Human hair follicle dermal papilla cells were seeded at a density of $2 \times 10^3$ cells/well on 96-well plates, followed by incubation overnight. After changing into serum-free medium, the cells were treated with the peptides, followed by incubation for 3 days, and then the wells were treated with 4 mg/ml MTT solution, followed by reaction for 4 hours. The resulting formazan was solubilized with DNSO, and then the absorbance was measured at 550 nm using a microplate reader. The results are shown in FIGS. 1a and 1b.

Figure 1B:
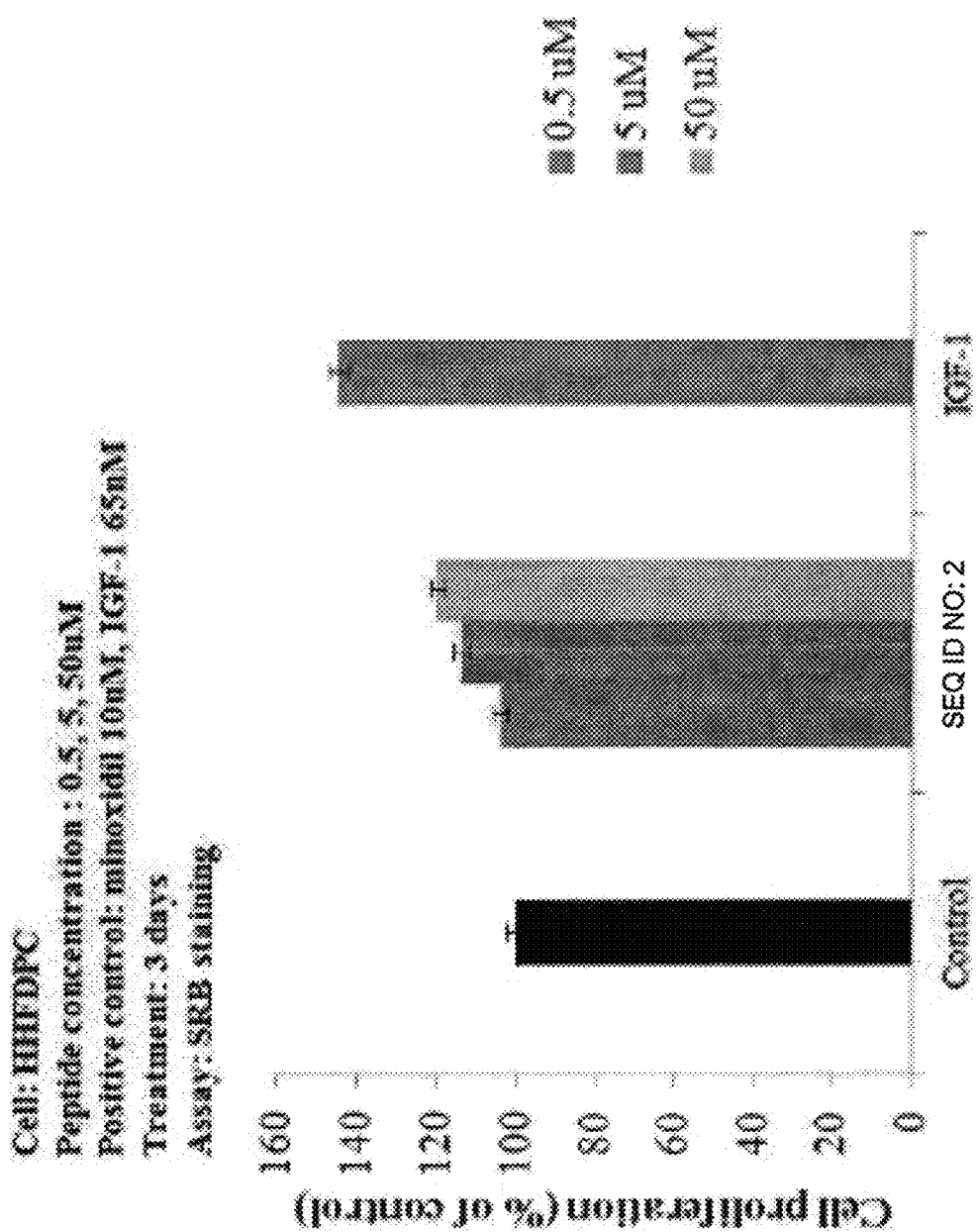
FIG. 1b is a graph showing a human hair follicle dermal papilla cell (HHFDPC) growth stimulating effect of a peptide composed of the amino acid sequence of SEQ ID NO: 2 according to an embodiment of the present invention.

As can be confirmed from FIGS. 1a and 1b, the growth of human hair follicle dermal papilla cells was stimulated in a dose-dependent manner by the treatment of the peptide composed of the amino acid sequence of SEQ ID NO: 1 or SEQ ID NO: 2, respectively.

Example 2: β-Catenin Activity Test

Human hair follicle dermal papilla cells were seeded at a density of $4 \times 10^5$ cells/well on 6-well plates, followed by incubation overnight. After changing into serum-free medium, the cells were treated with the peptides, followed by incubation for 15 and 30 minutes, and then the wells were harvested to isolate nuclear and cytoplasmic proteins. Western blotting was performed using β-catenin (Santa Cruz Biotechnology, USA) to compare β-catenin expression patterns. The results are shown in FIGS. 2a and 2b.

Figure 2B:
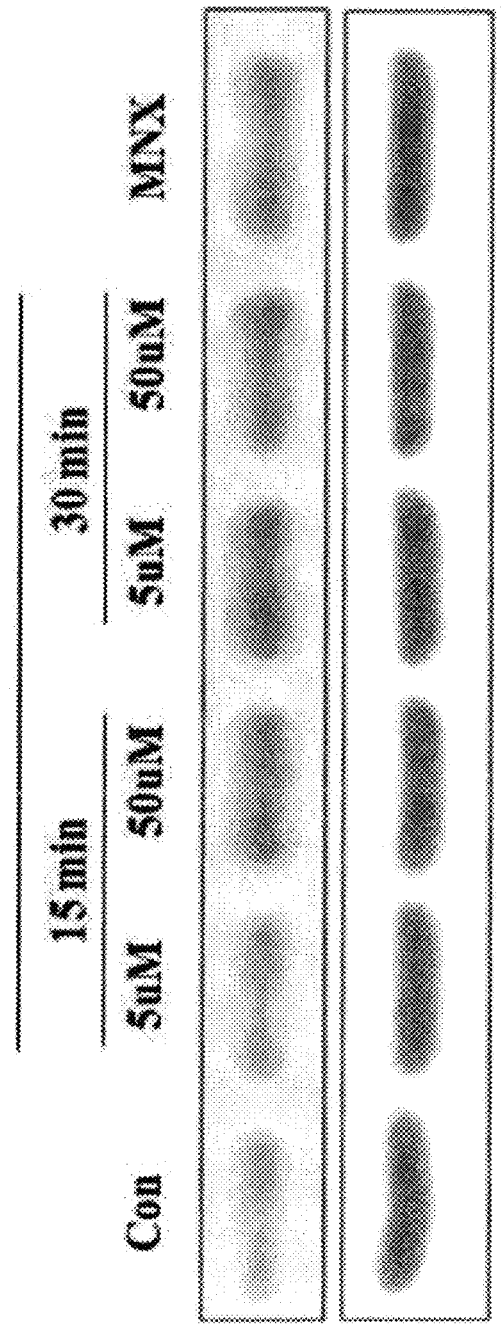
FIG. 2b is a diagram showing the results of confirming an increase in expression of β-catenin by a peptide composed of the amino acid sequence of SEQ ID NO: 2 according to an embodiment of the present invention.

As can be confirmed from FIGS. 2a and 2b, the activity of β-catenin, which is a hair growth-related factor, was increased in human hair follicle dermal papilla by the treatment with the peptide composed of the amino acid sequence of SEQ ID NO: 1 or SEQ ID NO: 2. The increase in expression of β-catenin and the activity thereof increase the expression of hair growth-related molecules.

Example 3: KGF and VEGF RT-PCR

Human hair follicle dermal papilla cells were seeded at a density of $4 \times 10^5$ cells/well on 6-well plate, followed by incubation overnight. After changing into serum-free medium, the cells were treated with the peptides, followed by incubation for 24 hours, and then the wells were harvested to isolate RNA. After RNA quantification, cDNA synthesis was conducted using the cDNA synthesis kit (Intron, Korea), followed by PCR using PCR premix (Intron, Korea) and respective KGF and VEGF primers, and then electrophoresis was performed on 5% agarose gel to compare the mRNA expression levels of the growth factors in sample treatment conditions. The results are shown in FIGS. 3a and 3b.

Figure 3A:
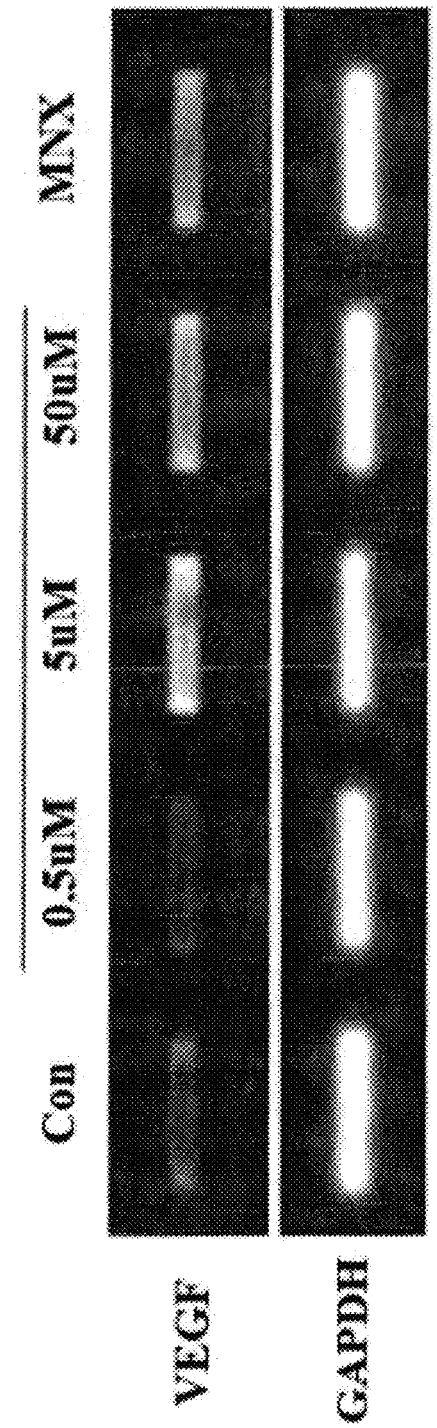
FIG. 3a is a diagram showing the results of confirming an increase in expression of VEGF by a peptide composed of the amino acid sequence of SEQ ID NO: 1 according to an embodiment of the present invention.

As can be confirmed from FIG. 3a, the expression of VEGF, which influences the growth of human hair follicle dermal papilla cells, was increased by the treatment with the peptide composed of the amino acid sequence of SEQ ID NO: 1.

Figure 3B:
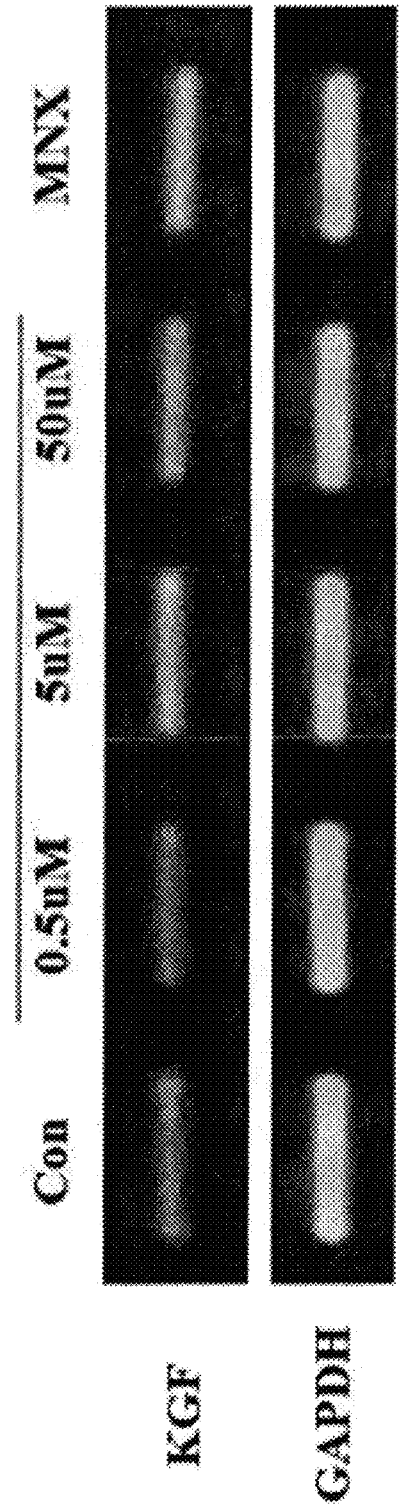
FIG. 3b is a diagram showing the results of confirming an increase in expression of KGF by a peptide composed of the amino acid sequence of SEQ ID NO: 2 according to an embodiment of the present invention.

As can be confirmed from FIG. 3b, the expression of KGF, which influences the growth of human hair follicle dermal papilla cells, was increased by the treatment with the peptide composed of the amino acid sequence of SEQ ID NO: 2.

Example 4: PI3K & p-ERK WB

Human hair follicle dermal papilla cells were seeded at a density of $4 \times 10^5$ cells/well on 6-well plate, followed by incubation overnight. After changing into serum-free medium, the cells were treated with the peptides, followed by incubation for 15 and 30 minutes, and then the wells were harvested to prepare cell lysate. Western blotting was performed using PI3K antibodies (Santa Cruz Biotechnology, USA) and phospho-ERK antibody (Cell Signaling Technology, USA) to compare protein expression patterns. The results are shown in FIGS. 4a and 4b.

Figure 4A:
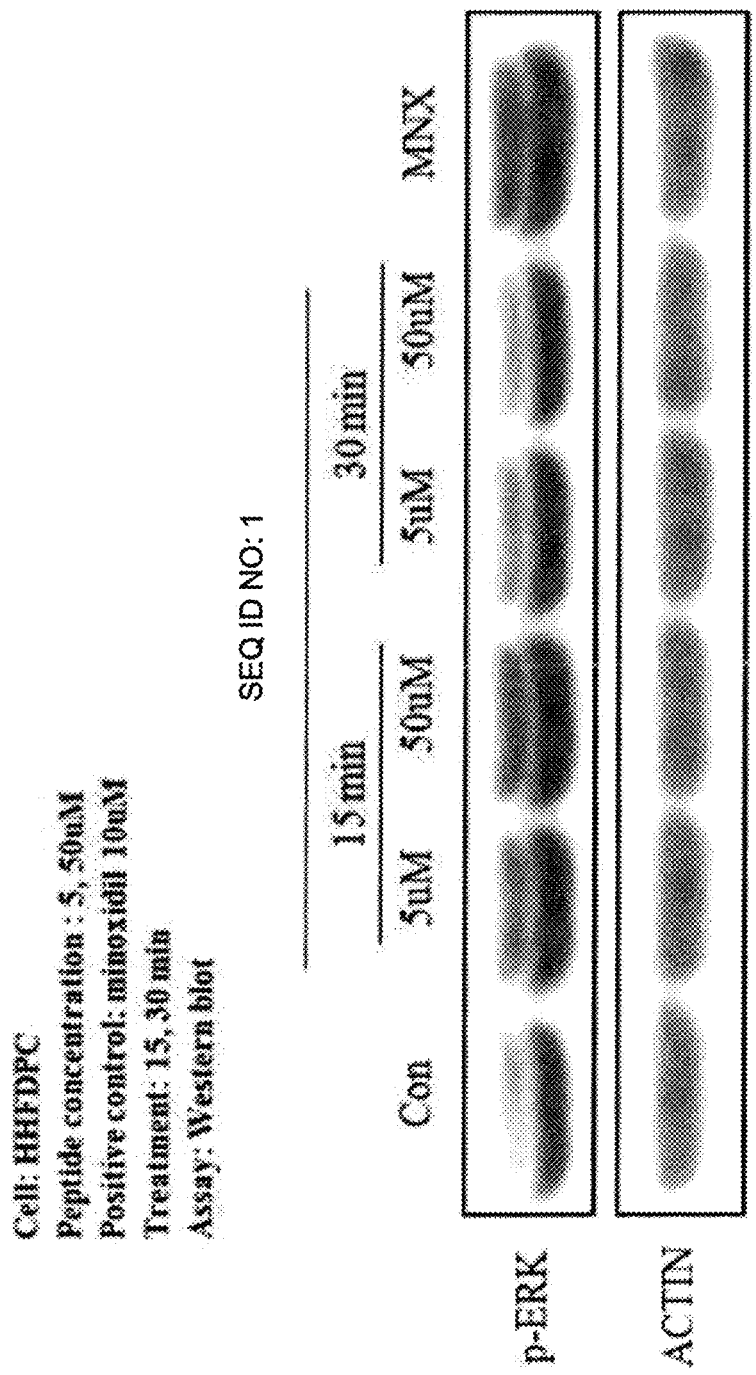
FIG. 4a is a diagram showing the results of confirming an increase in phosphorylation of EPK by a peptide composed of the amino acid sequence of SEQ ID NO: 1 according to an embodiment of the present invention.

As can be confirmed from FIG. 4a, the phosphorylation level of ERK, which influences the growth of human hair follicle dermal papilla cells, was increased by the treatment with a peptide composed of the amino acid sequence of SEQ ID NO: 1.

Figure 4B:
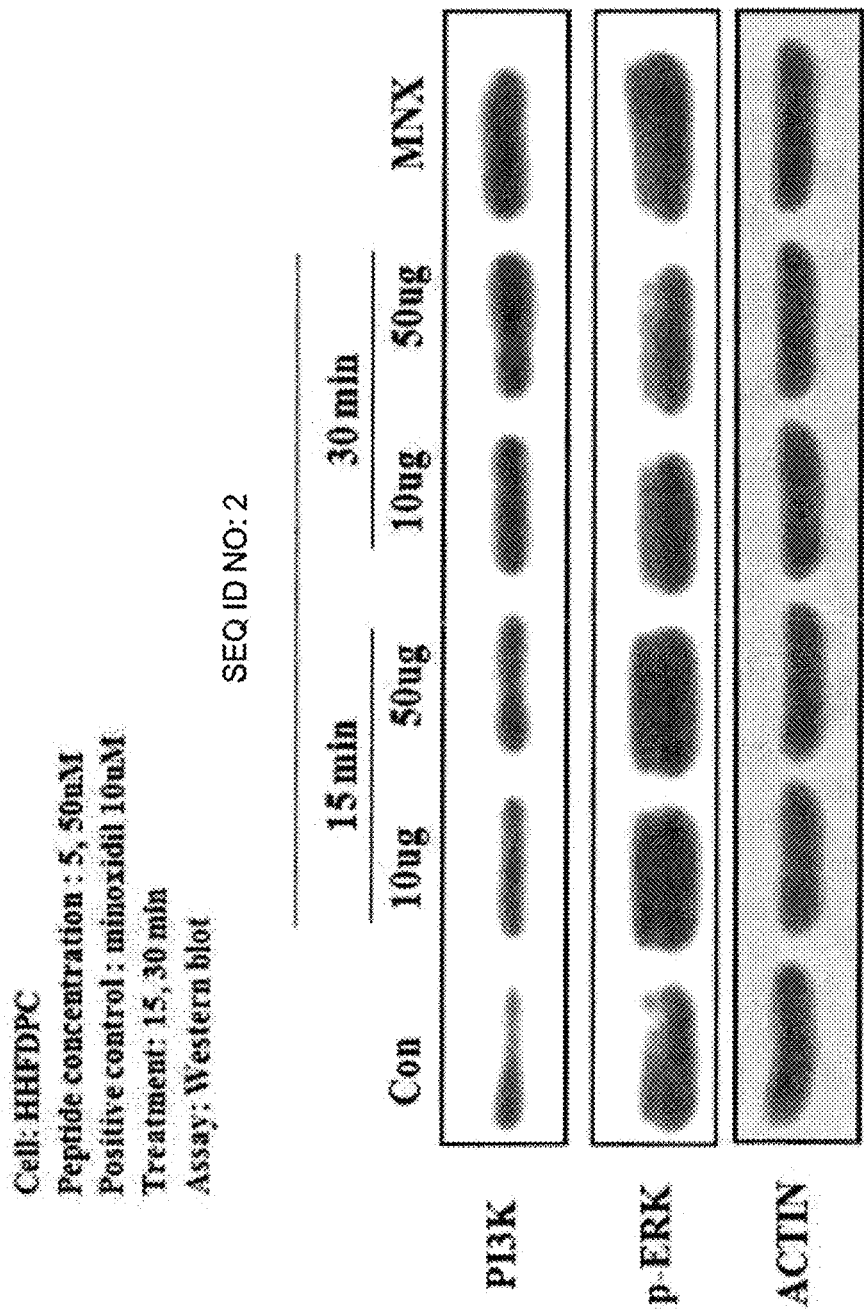
FIG. 4b is an image showing the results of confirming an increase in expression of PI3K and an increase in phosphorylation of ERK by a peptide composed of the amino acid sequence of SEQ ID NO: 2 according to an embodiment of the present invention.

In addition, as can be confirmed n FIG. 4b, the increase in expression of PI3K as a hair growth signaling molecule and the increase in phosphorylation level of ERK were observed in human hair follicle dermal papilla cells by the treatment with a peptide composed of the amino acid sequence of SEQ ID NO: 2.

Example 5: MSX2 RT-PCR

Human hair follicle dermal papilla cells were seeded at a density of $4 \times 10^5$ cells/well on 6-well plate, followed by incubation overnight. After changing into serum-free medium, the cells were treated with the peptides, followed by incubation for 24 hours, and then the wells were harvested to isolate RNA. After RNA quantification, cDNA synthesis was conducted using the cDNA synthesis kit (Intron, Korea), followed by PCR using PCR premix (Intron, Korea) and MSX2 primers, and then electrophoresis was performed on 5% agarose gel to compare the mRNA expression level of the growth factor in sample treatment conditions. The results are shown in FIG. 5.

TABLE 3

| SEQ ID NO | Primer name | Sequence (5'-3') |
|---|---|---|
| 7 | MSX2_F | AACACAAGACCAACCGGAAG |
| 8 | MSX2_R | GCAGCCATTTTCAGCTTTTC |

Figure 5:
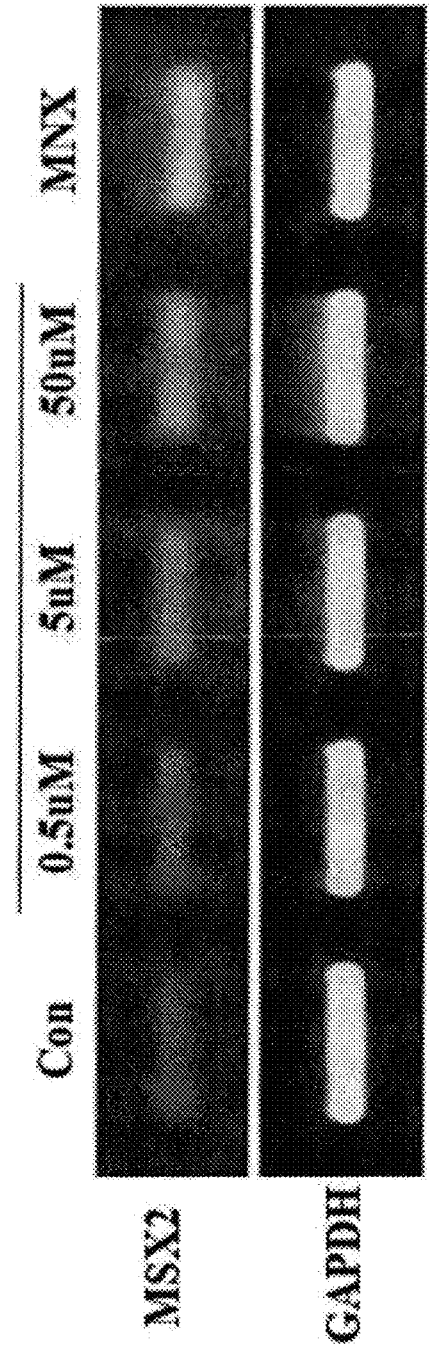
FIG. 5 is an image showing the results of confirming an increase in expression of MSX2 by a peptide composed of the amino acid sequence of SEQ ID NO: 1 according to an embodiment of the present invention.

As can be confirmed from FIG. 5, the expression of MSX2, which is a factor influencing the elongation of hair shafts, was increased in human hair follicle dermal papilla cells by the treatment with a peptide composed of the amino acid sequence of SEQ ID NO: 1.

Example 6: TGF-β1 RT-PCR

Human hair follicle dermal papilla cells were seeded at a density of $4 \times 10^5$ cells/well on 6-well plate, followed by incubation overnight. After changing into serum-free medium, the cells were treated with the peptides, followed by incubation for 24 hours, and then the wells were harvested to isolate RNA. After RNA quantification, cDNA synthesis was conducted using the cDNA synthesis kit (Intron, Korea), followed by PCR using PCR premix (Intron, Korea) and TGF-β1 primers, and then electrophoresis was performed on 5% agarose gel to compare the mRNA expression levels of the growth factors in respective sample treatment conditions. The results are shown in FIGS. 6a and 6b.

TABLE 4

| SEQ ID NO | Primer name | Sequence (5'-3') |
|---|---|---|
| 9 | TGF-β1_F | GCCCTGGATACCAACTATTGC |
| 10 | TGF-β1_R | TCAGCACTTGCAGGAGTAGCG |

Figure 6B:
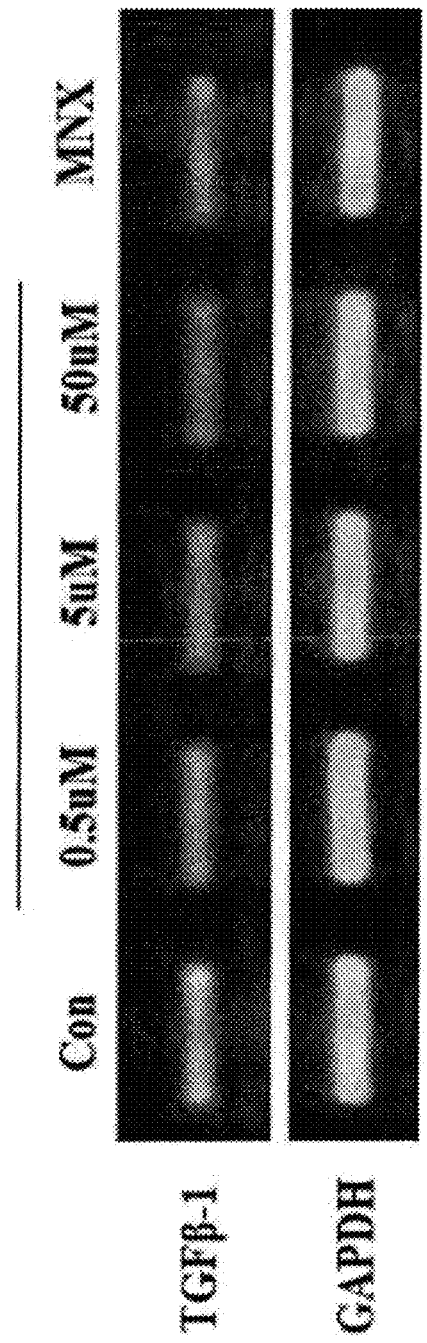
FIG. 6b is an image showing the results of confirming the inhibition of TGF-β1 expression by a peptide composed of the amino acid sequence of SEQ ID NO: 2 according to an embodiment of the present invention.

As can be seen from FIGS. 6a and 6b, the expression of TGF-β1, which is a hair growth inhibiting factor, was inhibited in human hair follicle dermal papilla cells by the treatment with the peptide composed of the amino acid sequence of SEQ ID NO: 1 or SEQ ID NO: 2.

Example 7: Bcl-2/Bax WB

Human hair follicle dermal papilla cells were seeded at a density of $4 \times 10^5$ cells/well on 6-well plate, followed by incubation overnight. After changing into serum-free medium, the cells were treated with the peptides, followed by incubation for 24 hours, and then the wells were harvested to prepare cell lysate. Western blotting was performed using Bcl-2 and Bax antibodies (Santa Cruz Biotechnology, USA) to compare protein expression patterns. The results are shown in FIGS. 7a and 7b.

As can be confirmed from FIGS. 7a and 7b, the expression of the anti-apoptotic protein Bcl-2 was increased and the expression of the apoptosis-related protein Bax was decreased in human hair follicle dermal papilla cells by the treatment with the peptide composed of the amino acid sequence of SEQ ID NO: 1 or SEQ ID NO: 2.

Example 8: Ha3-II and Keratin-14 RT-PCR

Figure 8B:
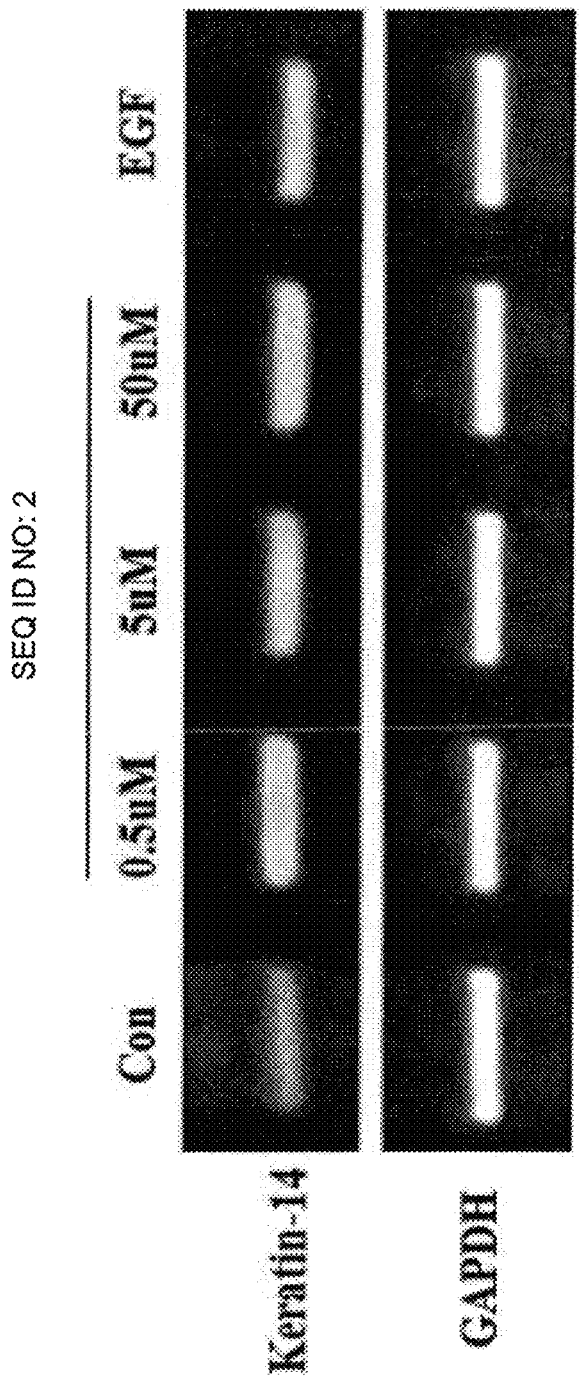
FIG. 8b is an image showing the results of confirming an increase in expression of keratin-14 by a peptide composed of the amino acid sequence of SEQ ID NO: 2 according to an embodiment of the present invention.

Human hair follicle dermal papilla cells were seeded at a density of $5 \times 10^5$ cells/well on 6-well plates, followed by incubation overnight. After changing into serum-free medium, the cells were treated with the peptides, followed by incubation for 24 hours, and then the wells were harvested to isolate RNA. After RNA quantification, cDNA synthesis was conducted using the cDNA synthesis kit (Intron, Korea), followed by PCR using PCR premix (Intron, Korea) and Ha3-II and keratin-14 primers, and then electrophoresis was performed on 5% agarose gel to compare the mRNA expression levels of the growth factors in respective sample treatment conditions. The results are shown in FIGS. 8a and 8b.

TABLE 5

| SEQ ID NO | Primer name | Sequence (5'-3') |
|---|---|---|
| 11 | Ha3-II_F | CAGAAGTATAGCAGTAAGACAG |
| 12 | Ha3-II_R | CAAGAGGAAAGTTTATTAGGC |
| 13 | Keratin-14_F | CCACCTTTCATCTTCCCAATTCTC |
| 14 | Keratin-14_R | GTGCGGATCTGGCGGTTG |

As can be confirmed from FIG. 8a, the mRNA expression of Ha3-II and keratin-14, which are hair growth-related factors, was increased in human hair follicle dermal papilla cells by the treatment with the peptide composed of the amino acid sequence of SEQ ID NO: 1.

As can be confirmed from FIG. 8b, the mRNA expression of keratin-14 was increased in human hair follicle dermal papilla cells by the treatment with the peptide composed of the amino acid sequence of SEQ ID NO: 2.

Example 9: DKK-1 RT-PCR

Human hair follicle dermal papilla cells were seeded at a density of $5 \times 10^5$ cells/well on 6-well plates, followed by incubation overnight. After changing into serum-free medium, the cells were treated with the peptides, followed by incubation for 24 hours, and then the wells were harvested to isolate RNA. After RNA quantification, cDNA synthesis was conducted using the cDNA synthesis kit (Intron, Korea), followed by PCR using PCR premix (Intron, Korea) and DKK-1 primers, and then electrophoresis was performed on 5% agarose gel to compare the mRNA expression levels of the growth factors in respective sample treatment conditions. The results are shown in FIGS. 9a and 9b.

TABLE 6

| SEQ ID NO | Primer name | Sequence (5'-3') |
|---|---|---|
| 15 | DKK-1_F | TGATGAGTACTGCGCTAGTC |
| 16 | DKK-1_R | CTCCTATGCTTGGTACACAC |

As can be confirmed from FIGS. 9a and 9b, the mRNA expression of DKK-1 as a hair growth delay-related factor, which has been increased by the treatment of human hair follicle dermal papilla cells with DHT, was decreased by the treatment with a peptide composed of the amino acid sequence of SEQ ID NO: 1 or SEQ ID NO: 2 according to an embodiment of the present invention.

Example 10: DKK-1 WB

Human hair follicle dermal papilla cells were seeded at a density of 4×10⁵ cells/well on 6-well plate, followed by incubation overnight. After changing into serum-free medium, the cells were treated with the peptides, followed by incubation for 24 hours, and then the wells were harvested to prepare cell lysate. Western blotting was performed using DKK-1 antibodies (Santa Cruz Biotechnology, USA) to compare protein expression patterns. The results are shown in FIGS. 10a and 10b.

Figure 10A:
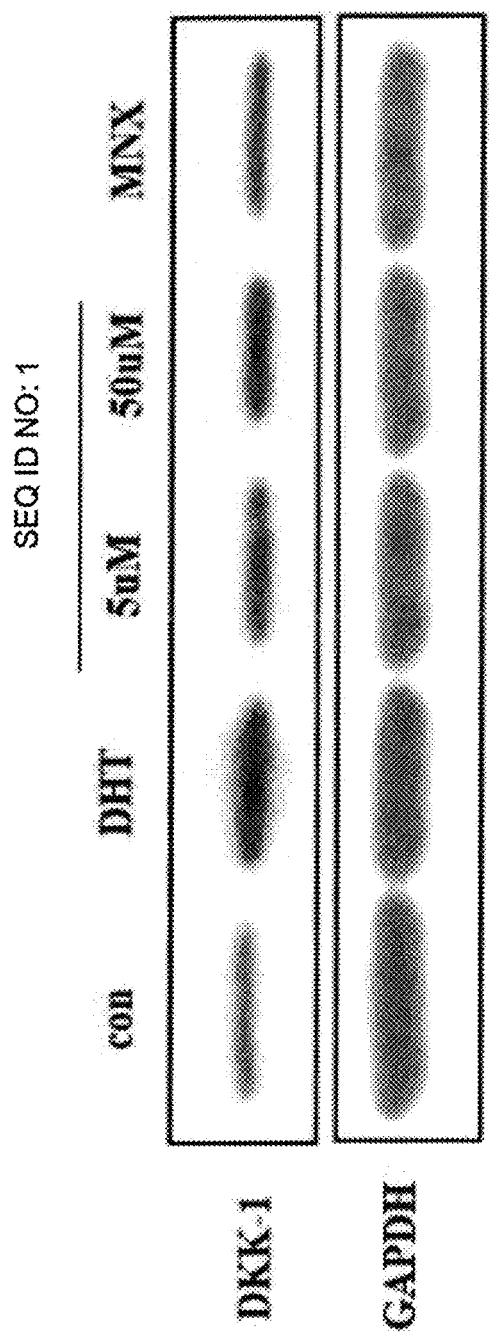
FIG. 10a is an image showing the results of confirming a decrease in expression of DKK-1 by a peptide composed of the amino acid sequence of SEQ ID NO: 1 according to an embodiment of the present invention.
Figure 10B:
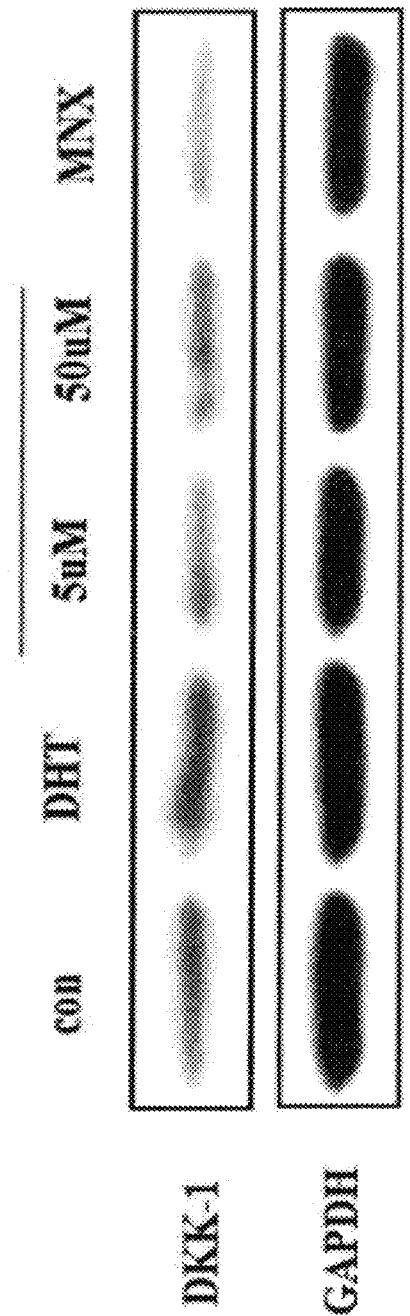
FIG. 10B is an image showing the results of confirming a decrease in expression of DKK-1 by a peptide composed of the amino acid sequence of SEQ ID NO: 2 according to an embodiment of the present invention.

As can be confirmed from FIGS. 10a and 10b, the protein expression of DKK-1 as a hair growth delay-related factor, which has been increased by the treatment of human hair follicle dermal papilla cells with DHT, was decreased by the treatment with a peptide composed of the amino acid sequence of SEQ ID NO: 1 or SEQ ID NO: 2 according to an embodiment of the present invention.

Example 11: Melanin Measurement Assay

After melanocytes (B16F10 cell line) in 6-well plates were cultured in an incubator at 37° C. for 24 hours, the medium of each plate was removed and exchanged with a fresh medium, followed by treatment with the present peptide with different concentrations. After the incubation for 72 hours, the culture medium was removed, and the cells were taken off and then transferred into 1.5-ml tubes, followed by centrifugation at 13,000 rpm for 3 minutes. The supernatant was removed, and cell pellets were collected to observe melanin. Then, 150 µl of 2 M NaOH was added to the cell pellets to lyse intracellular melanin at 60° C. for 30 minutes. Then, 100 µl of the supernatant obtained from the lysis was added into each well of 96-well plates, and the absorbance was measured at 490 nm. The results are shown in FIGS. 11a and 11b.

Figure 11A:
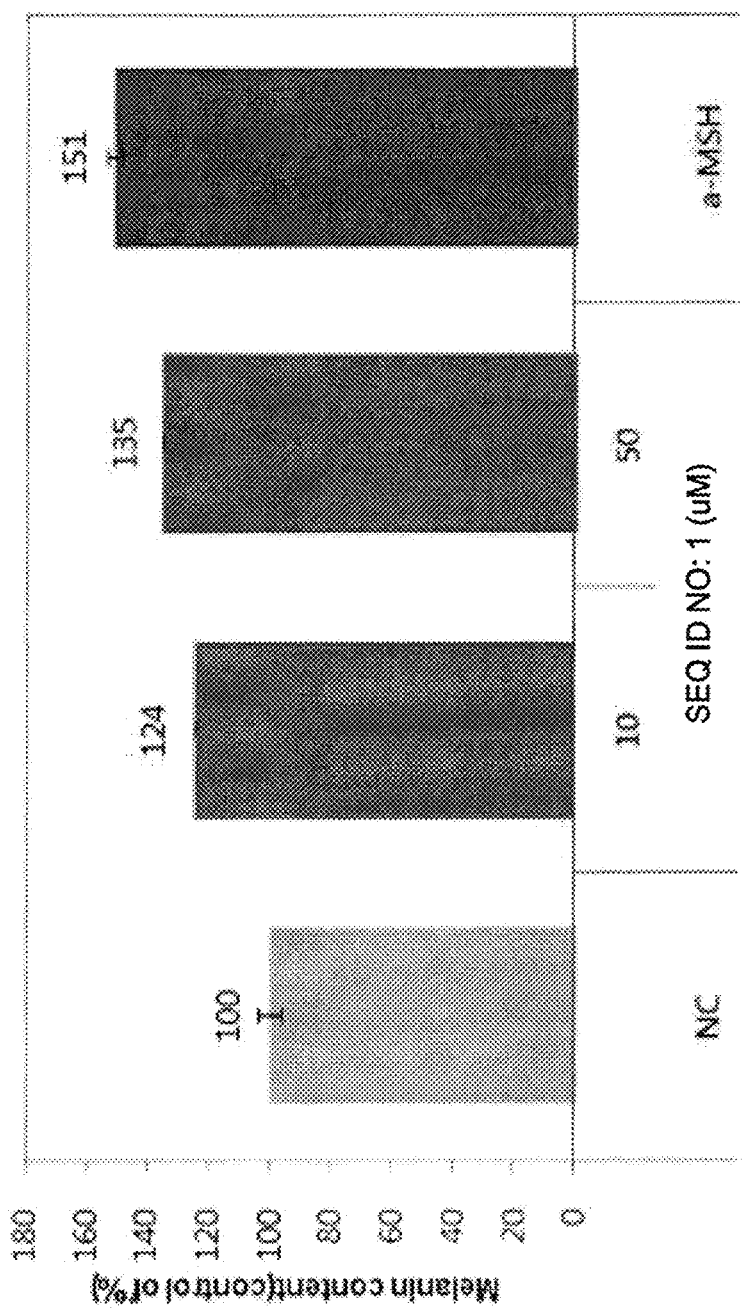
FIG. 11a is a diagram showing the results of confirming a melanogenesis increasing effect by a peptide composed of the amino acid sequence of SEQ ID NO: 1 according to an embodiment of the present invention.
Figure 11B:
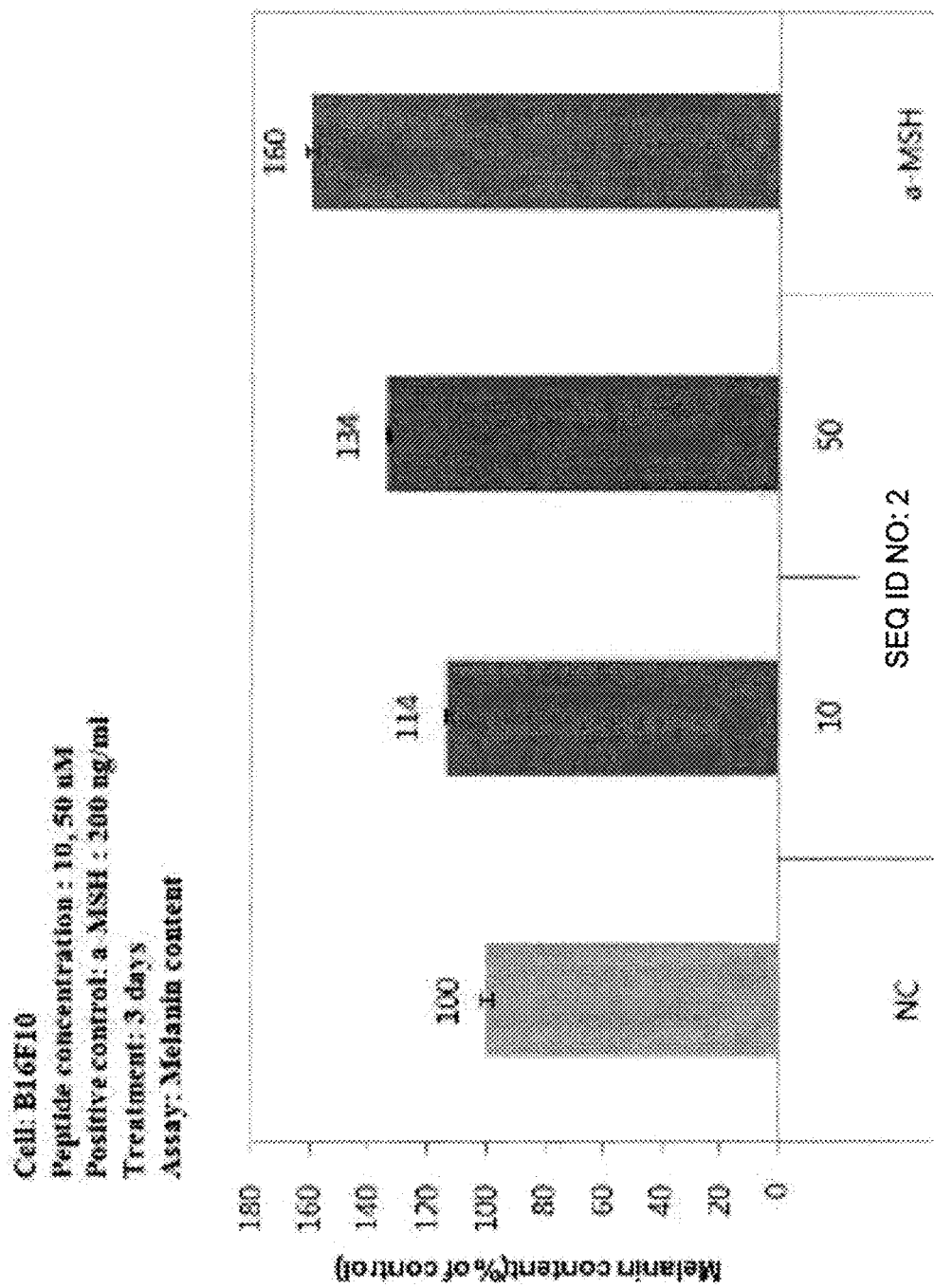
FIG. 11b is a diagram showing the results of confirming a melanogenesis increasing effect by a peptide composed of the amino acid sequence of SEQ ID NO: 2 according to an embodiment of the present invention.

As shown in FIGS. 11a and 11b, melanogenesis was increased in melanocytes by the treatment with the peptide composed of the amino acid sequence of SEQ ID NO: 1 or SEQ ID NO: 2.

Example 12: Tyrosinase Activity Assay

Melanoma cell line (B16F10) cells were cultured in 6-well culture plates for 24 hours, and treated with a peptide with difference concentrations, followed by culture for 72 hours. The 6-well culture plates were loaded on ice and washed with cool PBS, and then 300 µl of 0.1 M sodium phosphate buffer (pH 6.8 lysis buffer) containing 1% Triton X-100 was added. The cells were collected in 1.5-mL tubes, and then cell membranes were disrupted by repeating five times rapid-freezing at −270° C. and thawing. After centrifugation at 13,000 rpm for 20 minutes, the supernatant was collected in other 1.5-mL tubes, and the protein of the samples was quantified. The samples were diluted to have the same protein concentration and then dispensed in each three wells in a 96-well culture plate, and then 20 µl of 10 mM L-dopa was added, followed by incubation at 37° C. for 1 hour. The absorbance was measured at 475 nm, and the results are shown in FIGS. 12a and 12b.

Figure 12B:
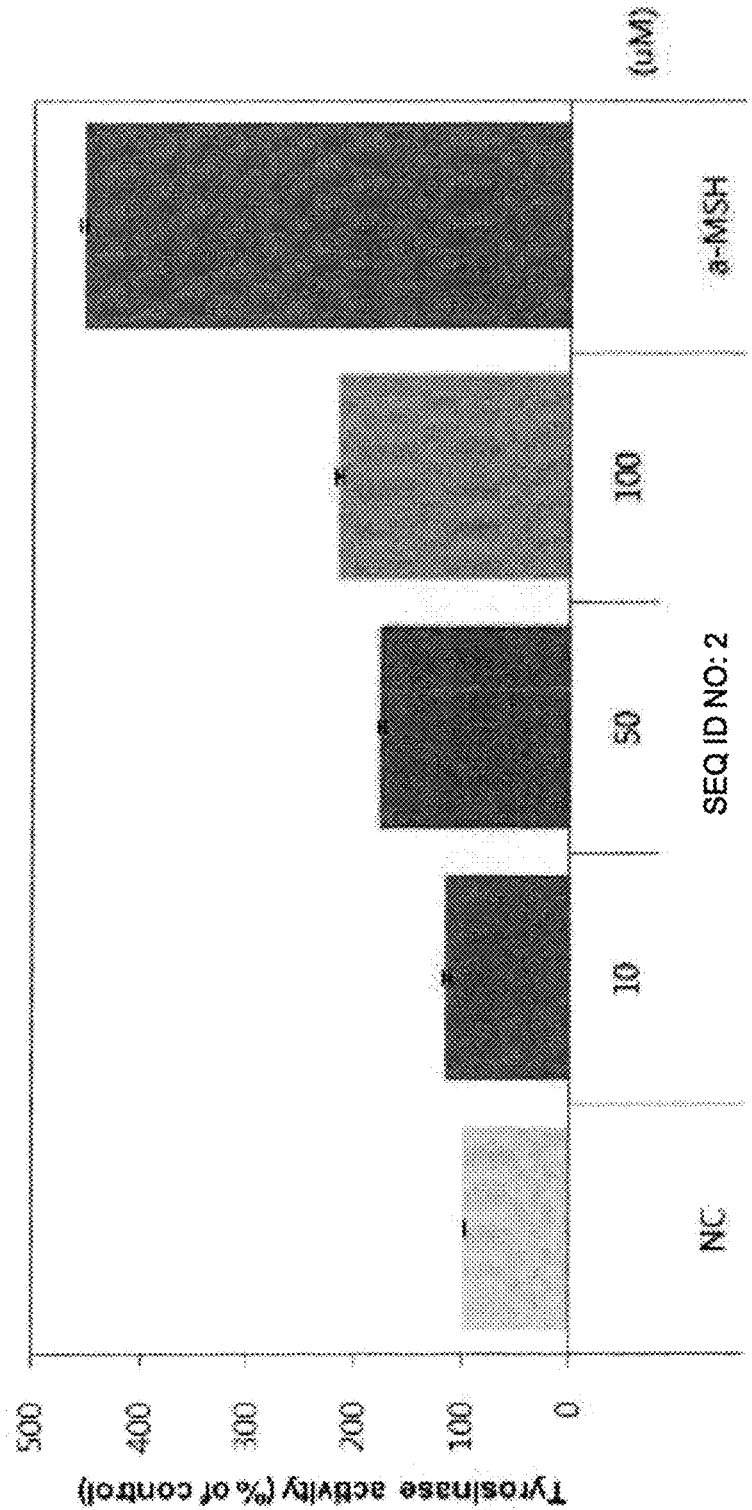
FIG. 12b shows the results of confirming the increase of tyrosinase activity by a peptide composed of the amino acid sequence of SEQ ID NO: 2 according to an embodiment of the present invention.

As shown in FIGS. 12a and 12b, tyrosinase activity was increased in melanocytes by the treatment with the peptide composed of the amino acid sequence of SEQ ID NO: 1 or SEQ ID NO: 2.

Example 13: Melanogenesis-Related Gene RT-PCR

Melanocytes (B16F10 cell line) were incubated on 6-well culture plates in an incubator for 24 hours, and were treated with the peptides of the present invention with different concentrations. After RNA was extracted from the cells incubated for 72 hours, cDNA was prepared. PCR was performed by using respective primers specific to MITF and tyrosinase, which are factors involved in melanogenesis, and the expression changes of the respective genes were observed. The results are shown in FIGS. 13a and 13b.

TABLE 7

| SEQ ID NO | Primer name | Sequence (5'-3') |
|---|---|---|
| 17 | MITF_F | CCAGCCTGGCGATCATGTCAT |
| 18 | MITF_R | GGTCTGGACAGGAGTTGCTG |
| 19 | tyrosinase_F | GGCCAGCTTTCAGGCAGAGG |
| 20 | tyrosinase_R | TGGTGCTTCATGGGCAAAAT |
| 21 | TRP1_F | TCTGTGAAGGTGTGCAGGAG |
| 22 | TRP1_R | CCGAAACAGAGTGGAAGGTT |

Figure 13A:
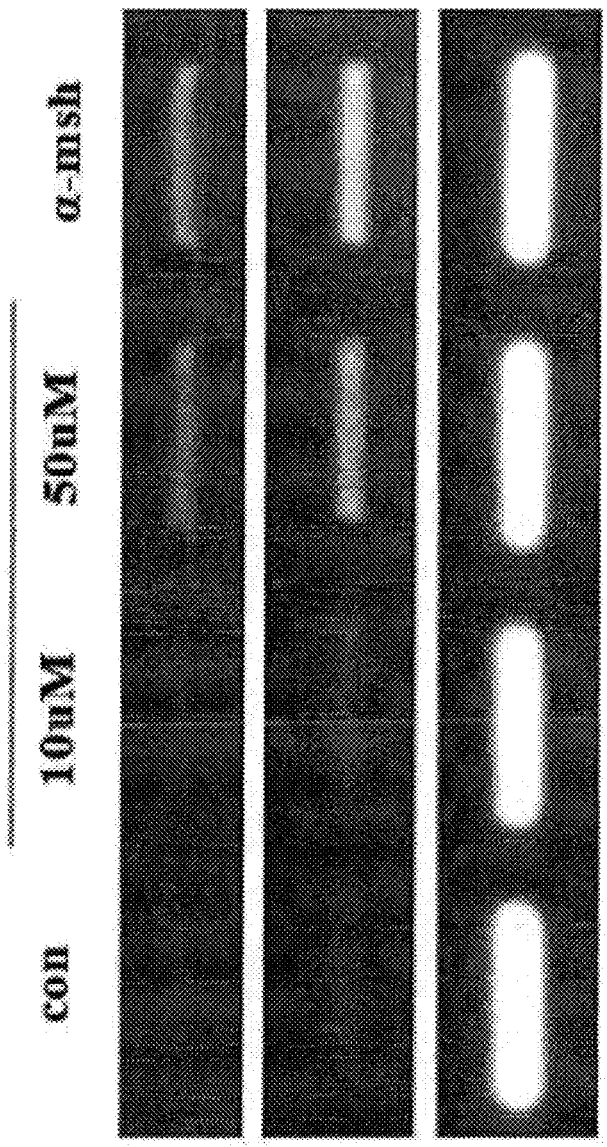
FIG. 13a shows the results of confirming increases in mRNA expression of MITF and tyrosinase by a peptide composed of the amino acid sequence of SEQ ID NO: 1 according to an embodiment of the present invention.
Figure 13B:
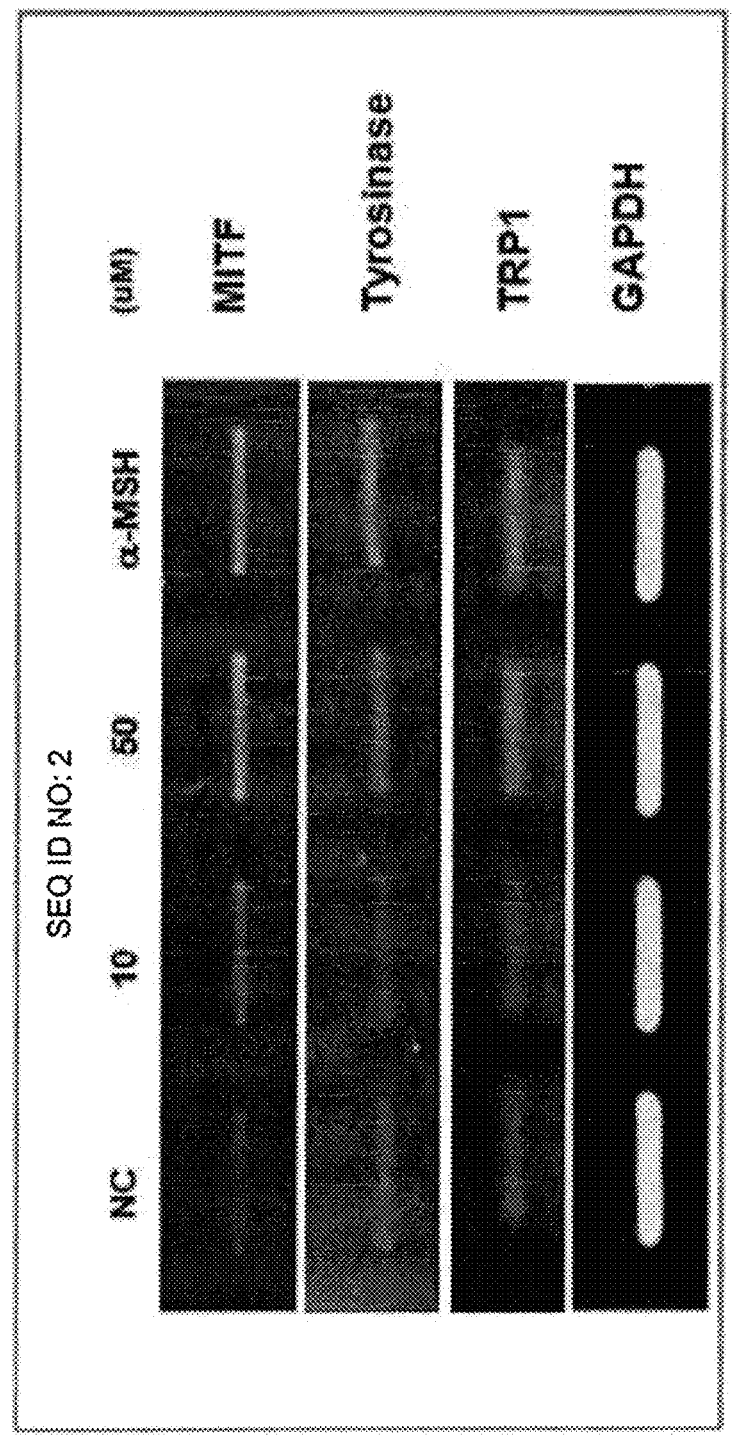
FIG. 13b shows the results of confirming increases in mRNA expression of MITF, tyrosinase, and TRP1 by a peptide composed of the amino acid sequence of SEQ ID NO: 1 according to an embodiment of the present invention.

As can be seen from FIG. 13a, the mRNA expression of MITF transcription factor and tyrosinase enzyme, which are involved in melanogenesis, was increased by the treatment of melanocytes with the peptide composed of the amino acid sequence of SEQ ID NO: 1.

As can be seen from FIG. 13b, the mRNA expression of MITF transcription factor and tyrosinase enzyme, which are involved in melanogenesis, was increased by the treatment of melanocytes with the peptide composed of the amino acid sequence of SEQ ID NO: 2.

Example 14: Melanogenesis-Related Protein Western Blotting

Melanocytes (B16F10 cell line) were incubated on 6-well culture plates for 24 hours, and were treated with the peptides of the present invention with different concentrations. After 72-hour incubation, the cells were lysed, and the cells were subjected to western blotting using specific antibodies (two types, both from Santa Cruz Biotechnology, USA) to investigate the expression of MITF and tyrosinase, which are factors involved in melanogenesis. The results are shown in FIG. 14.

Figure 14A:
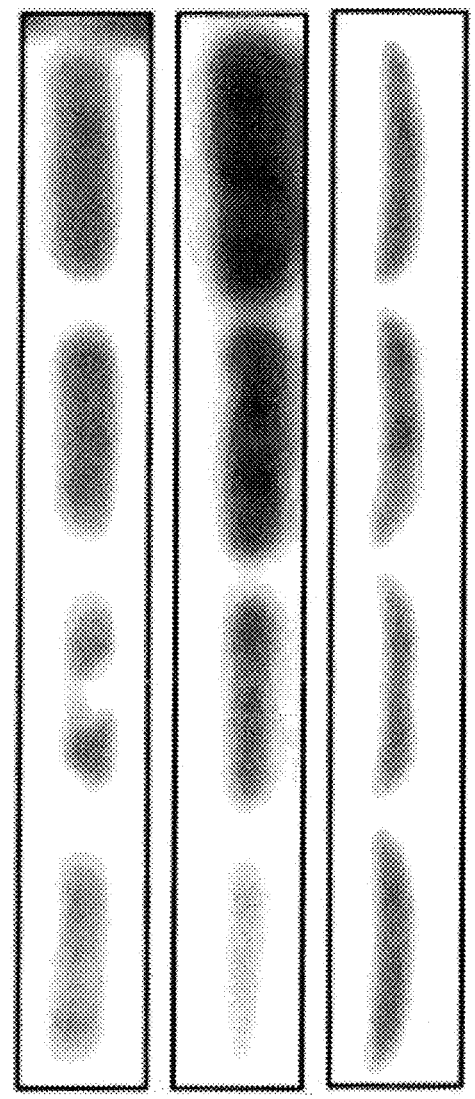
FIG. 14a is an image showing the results of confirming increases of protein expression of MITF and tyrosinase by a peptide composed of the amino acid sequence of SEQ ID NO: 1 according to an embodiment of the present invention.
Figure 14B:
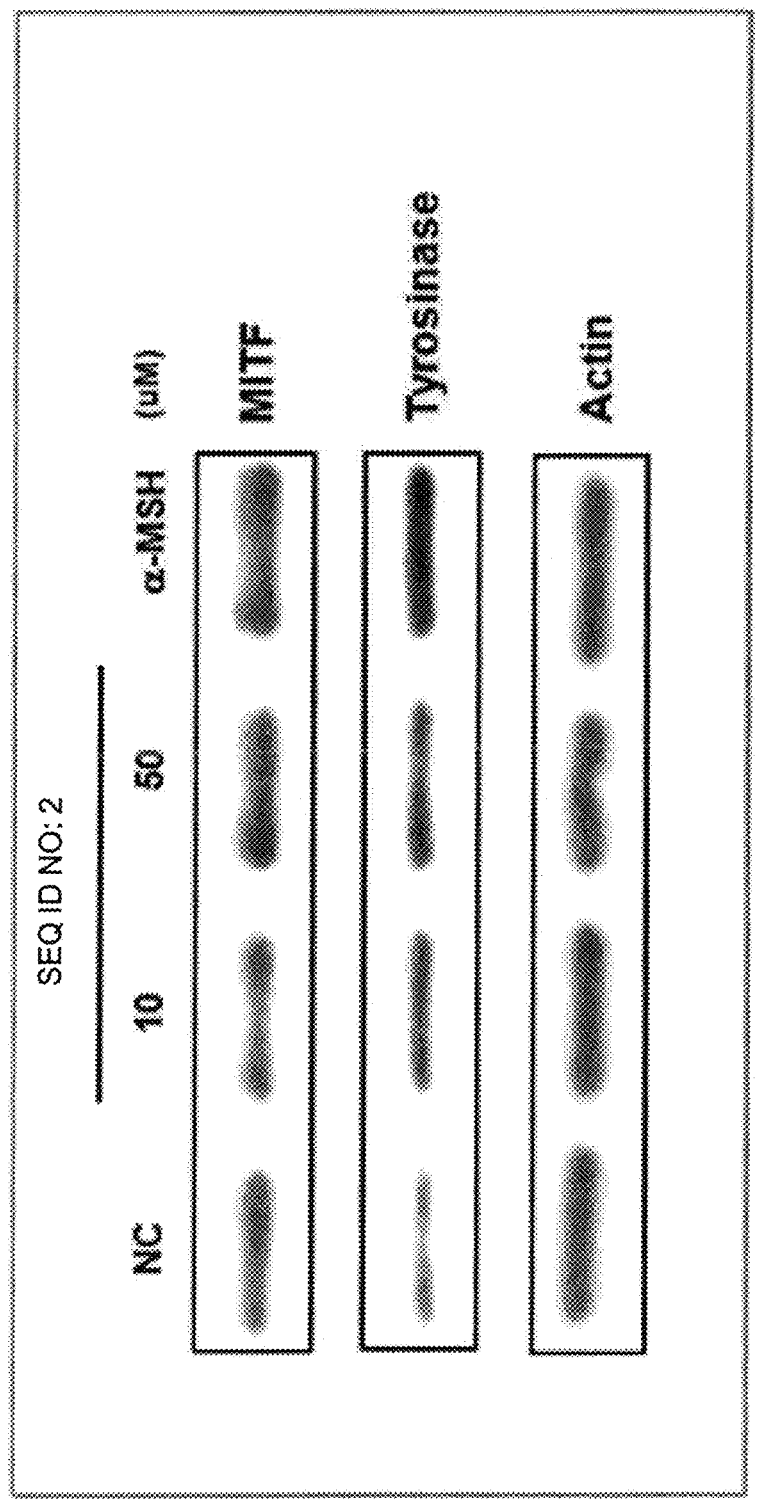
FIG. 14b is an image showing the results of confirming increases in protein expression of MITF and tyrosinase by a peptide composed of the amino acid sequence of SEQ ID NO: 2 according to an embodiment of the present invention.

As can be seen from FIG. 14a, the protein expression of MITF transcription factor and tyrosinase enzyme, which are involved in melanogenesis, was increased by the treatment of melanocytes with the peptide composed of the amino acid sequence of SEQ ID NO: 1.

Example 15: Melanogenesis-Related Protein Activity Assay

Melanocytes (B16F10 cell line) were incubated on 6-well culture plates in an incubator for 24 hours, and were treated with the peptide of the present invention with different concentrations. After 72-hour incubation, the cells were lysed, and the cells were subjected to western blotting using specific antibodies (Cell Signaling Technology, USA) to investigate the phosphorylation level of CREB, which is a signaling substance involved in melanogenesis.

As can be confirmed from FIG. 15, the phosphorylation level of CREB, which is a factor involved in melanogenesis, was increased when the melanocytes were treated with the peptide composed of the amino acid sequences of SEQ ID NO: 2.

INDUSTRIAL APPLICABILITY

The present invention relates to a peptide showing hair production stimulating activity and/or melanogenesis stimulating activity, a composition containing the peptide as an active ingredient for preventing and/or improving hair loss, a composition containing the peptide as an active ingredient for stimulating hair production and/or hair growth, a use of the peptide for preventing and/or improving hair loss, a use of the peptide for stimulating hair production and/or hair growth, a pharmaceutical composition containing the peptide as an active ingredient for preventing and/or treating hypomelanosis, a cosmetic composition containing the peptide as an active ingredient for preventing and/or improving hypomelanosis, and a use of the peptide for preventing, improving and/or treating hypomelanosis.

The invention claimed is:

1. A peptide having an activity to stimulate hair production or melanogenesis, the peptide consisting of the amino acid sequence of SEQ ID NO: 1 or SEQ ID NO: 2, optionally wherein (i) the C-terminal end of the peptide is modified by the presence of an amino group or an azide group, or (ii) the N-terminal end of the peptide comprises a protecting group.

2. The peptide of claim 1, wherein the peptide stimulates the growth of hair follicle cells.

3. The peptide of claim 1, wherein the peptide increases the expression of β-catenin.

4. The peptide of claim 1, wherein the peptide increases the expression of a hair production-related growth factor selected from the group consisting of keratinocyte growth factor (KGF) and vascular endothelial growth factor (VEGF).

5. The peptide of claim 1, wherein the peptide increases the expression of phosphoinositide 3-kinase (PI3K) and the phosphorylation of extracellular signal-regulated kinase (ERK).

6. The peptide of claim 1, wherein the peptide increases the expression of a hair production-related factor selected from the group consisting of Msh homeobox 2 (MSX2), Ha3-II (Keratin, type I cuticular Ha3-II), and keratin-14.

7. The peptide of claim 1, wherein the peptide decreases the expression of a hair growth delay factor selected from the group consisting of transforming growth factor beta 1 (TGF-β1) and Dickkopf WNT Signaling Pathway Inhibitor 1 (DKK-1).

8. The peptide of claim 1, wherein the peptide increases the expression of B-cell lymphoma 2 (Bcl-2) and decreases the expression of BCL2-associated X protein (Bax).

9. The peptide of claim 1, wherein the peptide increases the activity of tyrosinase.

10. The peptide of claim 1, wherein the peptide increases the expression of a melanin synthesis-related factor selected from the group consisting of microphthalmia-associated transcription factor (MITF) and tyrosinase-related protein 1 (TRP1).

11. The peptide of claim 1, wherein the peptide increases the expression of tyrosinase.

12. The peptide of claim 1, wherein the peptide increases the phosphorylation of cAMP response element-binding protein (CREB).

13. A method for preventing or improving hair loss in a subject comprising:
administering a composition comprising at least one peptide selected from the peptide consisting of the amino acid of SEQ ID NO: 1 and peptide consisting of the amino acid of SEQ ID NO: 2 to the subject, as an active ingredient.

14. A method for stimulating hair production or hair growth in a subject comprising:
  administering a composition comprising at least one peptide selected from the peptide consisting of the amino acid of SEQ ID NO: 1 and peptide consisting of the amino acid of SEQ ID NO: 2 to the subject, as an active ingredient.

15. A method for preventing or treating hypomelanosis in a subject comprising:
  administering a pharmaceutical composition comprising at least one peptide selected from the peptide consisting of the amino acid of SEQ ID NO: 1 and peptide consisting of the amino acid of SEQ ID NO: 2 to the subject, as an active ingredient.

16. The method of claim 15, wherein the hypomelanosis is vitiligo, albinism, nevus depigmentosus, *pityriasis* alba, *pityriasis versicolor*, post-inflammatory depigmentation, morphea, piebaldism, idiopathic guttate hypomelanosis, or leucoderma punctatum.

17. A method for preventing or improving hypomelanosis in a subject comprising:
  contacting the skin of a subject with a cosmetic composition comprising at least one peptide selected from the peptide consisting of the amino acid of SEQ ID NO: 1 and peptide consisting of the amino acid of SEQ ID NO: 2, as an active ingredient.

18. The method of claim 17, wherein the hypomelanosis is vitiligo, albinism, nevus depigmentosus, *pityriasis* alba, *pityriasis versicolor*, post-inflammatory depigmentation, morphea, piebaldism, idiopathic guttate hypomelanosis, or leucoderma punctatum.

19. A pharmaceutical composition comprising a peptide consisting of the amino acid sequence of SEQ ID NO: 1 or SEQ ID NO: 2, optionally wherein (i) the C-terminal end of the peptide is modified by the presence of an amino group or an azide group, or (ii) the N-terminal end of the peptide comprises a protecting group.

20. The peptide of claim 1, wherein the C-terminal end of the peptide is modified by the presence of an amino group or an azide group.

21. The peptide of claim 1, wherein the N-terminal end of the peptide comprises a protecting group.

22. The peptide of claim 21, wherein the protecting group is selected from the group consisting of an acetyl group, a fluorenyl methoxy carbonyl group, a formyl group, a palmitoyl group, a myristyl group, a stearyl group, and polyethylene glycol (PEG) to the N-terminal of the peptide.

* * * * *

SEQUENCE LISTING

```
<160> NUMBER OF SEQ ID NOS: 22

<210> SEQ ID NO 1
<211> LENGTH: 9
<212> TYPE: PRT
<213> ORGANISM: Artificial Sequence
<220> FEATURE:
<223> OTHER INFORMATION: Synthetic Construct

<400> SEQUENCE: 1

Trp Lys Trp Arg Ser Ala Asp Thr Leu
1               5

<210> SEQ ID NO 2
<211> LENGTH: 9
<212> TYPE: PRT
<213> ORGANISM: Artificial Sequence
<220> FEATURE:
<223> OTHER INFORMATION: Synthetic Construct

<400> SEQUENCE: 2

Lys Trp Lys Arg Ser Ala Asp Thr Leu
1               5

<210> SEQ ID NO 3
<211> LENGTH: 22
<212> TYPE: DNA
<213> ORGANISM: Artificial Sequence
<220> FEATURE:
<223> OTHER INFORMATION: Synthetic Construct

<400> SEQUENCE: 3
tctgtcgaac acagtggtac ct                                              22

<210> SEQ ID NO 4
<211> LENGTH: 23
<212> TYPE: DNA
<213> ORGANISM: Artificial Sequence
<220> FEATURE:
<223> OTHER INFORMATION: Synthetic Construct

<400> SEQUENCE: 4
gtgtgtccat ttagctgatg cat                                             23

<210> SEQ ID NO 5
<211> LENGTH: 21
<212> TYPE: DNA
<213> ORGANISM: Artificial Sequence
<220> FEATURE:
<223> OTHER INFORMATION: Synthetic Construct

<400> SEQUENCE: 5
ccatgaactt tctgctgtct t                                               21

<210> SEQ ID NO 6
```

```
<211> LENGTH: 21
<212> TYPE: DNA
<213> ORGANISM: Artificial Sequence
<220> FEATURE:
<223> OTHER INFORMATION: Synthetic Construct

<400> SEQUENCE: 6
tcgatcgttc tgtatcagtc t                                              21

<210> SEQ ID NO 7
<211> LENGTH: 20
<212> TYPE: DNA
<213> ORGANISM: Artificial Sequence
<220> FEATURE:
<223> OTHER INFORMATION: Synthetic Construct

<400> SEQUENCE: 7
aacacaagac caaccggaag                                                20

<210> SEQ ID NO 8
<211> LENGTH: 20
<212> TYPE: DNA
<213> ORGANISM: Artificial Sequence
<220> FEATURE:
<223> OTHER INFORMATION: Synthetic Construct

<400> SEQUENCE: 8
gcagccattt tcagcttttc                                                20

<210> SEQ ID NO 9
<211> LENGTH: 21
<212> TYPE: DNA
<213> ORGANISM: Artificial Sequence
<220> FEATURE:
<223> OTHER INFORMATION: Synthetic Construct

<400> SEQUENCE: 9
gccctggata ccaactattg c                                              21

<210> SEQ ID NO 10
<211> LENGTH: 21
<212> TYPE: DNA
<213> ORGANISM: Artificial Sequence
<220> FEATURE:
<223> OTHER INFORMATION: Synthetic Construct

<400> SEQUENCE: 10
tcagcacttg caggagtagc g                                              21

<210> SEQ ID NO 11
<211> LENGTH: 22
<212> TYPE: DNA
<213> ORGANISM: Artificial Sequence
<220> FEATURE:
<223> OTHER INFORMATION: Synthetic Construct

<400> SEQUENCE: 11
cagaagtata gcagtaagac ag                                             22

<210> SEQ ID NO 12
<211> LENGTH: 21
<212> TYPE: DNA
<213> ORGANISM: Artificial Sequence
<220> FEATURE:
<223> OTHER INFORMATION: Synthetic Construct

<400> SEQUENCE: 12
```

-continued

| | |
|---|---|
| caagaggaaa gtttattagg c | 21 |

<210> SEQ ID NO 13
<211> LENGTH: 24
<212> TYPE: DNA
<213> ORGANISM: Artificial Sequence
<220> FEATURE:
<223> OTHER INFORMATION: Synthetic Construct

<400> SEQUENCE: 13

| | |
|---|---|
| ccacctttca tcttcccaat tctc | 24 |

<210> SEQ ID NO 14
<211> LENGTH: 18
<212> TYPE: DNA
<213> ORGANISM: Artificial Sequence
<220> FEATURE:
<223> OTHER INFORMATION: Synthetic Construct

<400> SEQUENCE: 14

| | |
|---|---|
| gtgcggatct ggcggttg | 18 |

<210> SEQ ID NO 15
<211> LENGTH: 20
<212> TYPE: DNA
<213> ORGANISM: Artificial Sequence
<220> FEATURE:
<223> OTHER INFORMATION: Synthetic Construct

<400> SEQUENCE: 15

| | |
|---|---|
| tgatgagtac tgcgctagtc | 20 |

<210> SEQ ID NO 16
<211> LENGTH: 20
<212> TYPE: DNA
<213> ORGANISM: Artificial Sequence
<220> FEATURE:
<223> OTHER INFORMATION: Synthetic Construct

<400> SEQUENCE: 16

| | |
|---|---|
| ctcctatgct tggtacacac | 20 |

<210> SEQ ID NO 17
<211> LENGTH: 21
<212> TYPE: DNA
<213> ORGANISM: Artificial Sequence
<220> FEATURE:
<223> OTHER INFORMATION: Synthetic Construct

<400> SEQUENCE: 17

| | |
|---|---|
| ccagcctggc gatcatgtca t | 21 |

<210> SEQ ID NO 18
<211> LENGTH: 20
<212> TYPE: DNA
<213> ORGANISM: Artificial Sequence
<220> FEATURE:
<223> OTHER INFORMATION: Synthetic Construct

<400> SEQUENCE: 18

| | |
|---|---|
| ggtctggaca ggagttgctg | 20 |

<210> SEQ ID NO 19
<211> LENGTH: 20
<212> TYPE: DNA

```
<213> ORGANISM: Artificial Sequence
<220> FEATURE:
<223> OTHER INFORMATION: Synthetic Construct

<400> SEQUENCE: 19
ggccagcttt caggcagagg                                                   20

<210> SEQ ID NO 20
<211> LENGTH: 20
<212> TYPE: DNA
<213> ORGANISM: Artificial Sequence
<220> FEATURE:
<223> OTHER INFORMATION: Synthetic Construct

<400> SEQUENCE: 20
tggtgcttca tgggcaaaat                                                   20

<210> SEQ ID NO 21
<211> LENGTH: 20
<212> TYPE: DNA
<213> ORGANISM: Artificial Sequence
<220> FEATURE:
<223> OTHER INFORMATION: Synthetic Construct

<400> SEQUENCE: 21
tctgtgaagg tgtgcaggag                                                   20

<210> SEQ ID NO 22
<211> LENGTH: 20
<212> TYPE: DNA
<213> ORGANISM: Artificial Sequence
<220> FEATURE:
<223> OTHER INFORMATION: Synthetic Construct

<400> SEQUENCE: 22
ccgaaacaga gtggaaggtt                                                   20
```